United States Patent
Matsunaga et al.

(10) Patent No.: US 6,547,834 B1
(45) Date of Patent: Apr. 15, 2003

(54) HAIR DYE COMPOSITION

(75) Inventors: Kenichi Matsunaga, Sumida-ku (JP); Hajime Miyabe, Sumida-ku (JP); Yukihiro Ohashi, Sumida-ku (JP); Shintaro Totoki, Sumida-ku (JP); Yoshinori Saito, Sumida-ku (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/808,354

(22) Filed: Mar. 15, 2001

(30) Foreign Application Priority Data

Mar. 17, 2000 (JP) .................................. 2000-076636
Jun. 27, 2000 (JP) .................................. 2000-193185

(51) Int. Cl.⁷ .................................................. A61K 7/13
(52) U.S. Cl. ........................ 8/405; 8/405; 8/406; 8/409; 8/426
(58) Field of Search .................. 8/405, 406, 409, 8/426

(56) References Cited

U.S. PATENT DOCUMENTS

| | | | | |
|---|---|---|---|---|
| 4,168,144 A | | 9/1979 | Curry et al. .................. | 8/10.1 |
| 4,246,404 A | * | 1/1981 | Gertisser .................... | 542/466 |
| 4,344,879 A | | 8/1982 | Mohr et al. .................. | 260/146 |
| 4,403,095 A | | 9/1983 | Zink .......................... | 542/466 |
| 4,600,776 A | * | 7/1986 | Meisel et al. ............... | 544/198 |
| 5,445,672 A | | 8/1995 | Closs et al. ................. | 106/462 |
| 5,474,578 A | | 12/1995 | Chan et al. ................... | 8/431 |
| 5,725,607 A | | 3/1998 | Giera et al. .................. | 8/654 |
| 5,733,343 A | | 3/1998 | Moeckli ....................... | 8/426 |
| 5,879,413 A | | 3/1999 | Rondeau et al. ............... | 8/411 |
| 5,888,252 A | | 3/1999 | Moeckli ....................... | 8/426 |
| 5,980,587 A | | 11/1999 | Samain ........................ | 8/426 |
| 6,024,768 A | * | 2/2000 | Bittner et al. ................ | 8/410 |

FOREIGN PATENT DOCUMENTS

| | | |
|---|---|---|
| DE | 31 49 047 | 6/1983 |
| DE | 32 05 647 | 8/1983 |
| DE | 38 29 870 | 4/1989 |
| DE | 197 32 016 | 1/1999 |
| EP | 0 037 374 | 10/1981 |
| FR | 2 773 471 | 7/1999 |
| JP | 48-923 | 1/1973 |
| JP | 49-10215 | 1/1974 |
| JP | 49-4530 | 2/1974 |
| JP | 49-4531 | 2/1974 |
| JP | 50-5683 | 1/1975 |
| JP | 51-35405 | 10/1976 |
| JP | 54-111526 | 8/1979 |
| JP | 54-149731 | 11/1979 |
| JP | 56-76457 | 6/1981 |
| JP | 56-145952 | 11/1981 |
| JP | 6-271435 | 9/1994 |
| JP | 7-3177 | 1/1995 |
| JP | 7-166079 | 6/1995 |
| JP | 8-501322 | 2/1996 |
| JP | 8-507545 | 8/1996 |
| JP | 9-12914 | 1/1997 |
| JP | 10-502946 | 3/1998 |
| JP | 10-194942 | 7/1998 |
| WO | WO 88/00184 | 1/1988 |
| WO | WO 95/01772 | 1/1995 |
| WO | WO 99/20235 | 4/1999 |

\* cited by examiner

*Primary Examiner*—Yogendra N. Gupta
*Assistant Examiner*—Eisa B Elhilo
(74) *Attorney, Agent, or Firm*—Oblon, Spivak, McClelland, Maier & Neustadt, P.C.

(57) ABSTRACT

A hair dye composition containing a direct dye (1)

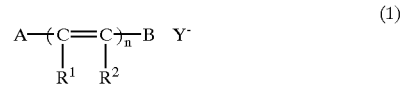

(1)

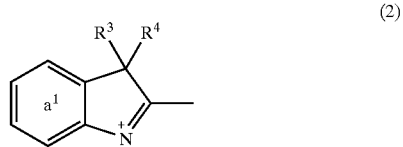

(2)

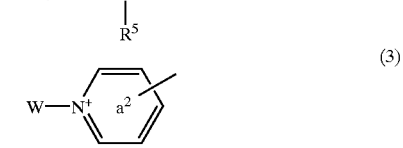

(3)

wherein, $R^1$, $R^2$ represents H or a lower alkyl group, A represents a group (2) or (3) and wherein B represents a group $-Z^1$, $-NR^8-Z^1$ or $-CH=Z^2$.

20 Claims, No Drawings

HAIR DYE COMPOSITION

TECHNICAL FIELD

The present invention relates to a hair dye composition featuring markedly high dyeing power, less color fade over time and a smaller color tone change of the dye even after storage.

BACKGROUND ART

Hair dyes can be classified by the dye to be used therefor, or whether they have bleaching action of melanin or not. Typical examples include a two-part permanent hair dye composed of a first part containing an alkali agent, an oxidation dye and a direct dye such as nitro dye and a second part containing an oxidizing agent; and one-part semi-permanent hair dye containing an organic acid or an alkali agent, and a direct dye such as acid dye, basic dye or nitro dye.

The above-described permanent hair dye is however accompanied with the drawbacks that color tone imparted by an oxidation dye is not so vivid and the color of the hair dyed with a vivid-color producing nitro dye ordinarily employed as a direct dye markedly fades over time and becomes dull soon even if the color tone rightly after dyeing is very vivid (Japanese Patent Application Laid-Open (Kokai) No. Hei 6-271435).

Recently, hair dyes containing as a direct dye a so-called cationic dye having a cation group contained in their conjugate system have been reported (Japanese Language Laid-Open Publication (PCT) No. Hei 8-507545, 8-501322 or 10-502946, or Japanese Patent Application Laid-Open (Kokai) No. Hei 10-194942). They have been found to involve drawbacks that intended dyeing effects are not available owing to decomposition of them caused by mixing, upon hair dyeing, with hydrogen peroxide ordinarily employed as an oxidizing agent; and that when the cation group is incorporated in an azo(—N=N)-based conjugated system, they are unstable to an alkali agent or a reducing agent essentially contained in a permanent hair dye.

DISCLOSURE OF THE INVENTION

An object of the present invention is to provide a hair dye composition featuring high hair dyeing power, less color fade over time and excellent storage stability to permit only a smaller color tone change of the dye after storage.

The present inventors have found that a hair composition containing a cationic dye represented by the below-described formula (1) which is disclosed as a dye for dyeing or printing fiber materials therewith in Japanese Patent Application Laid-Open (Kokai) No. Hei 7-166079, Japanese Patent Application Laid-Open (Kokai) No. Sho 54-111526, Japanese Patent Application Laid-Open (Kokai) No. Sho 49-10215, Japanese Patent Application Laid-Open (Kokai) No. Sho 48-923, Japanese Patent Application Laid-Open (Kokai) No. Sho 56-76457, Japanese Patent Application Laid-Open (Kokai) No. Sho 56-145952, Japanese Patent Application Laid-Open (Kokai) No. Hei 7-3177, U.S. Pat. No. 4,600,776, Japanese Patent Application Laid-Open (Kokai) No. Hei 9-12914, German Offenlegungsschrift DE-3149047, German Offenlegungsschrift DE-3205647, Japanese Patent Publication No. Sho 51-35405, Japanese Patent Publication No. Sho 49-4531, Japanese Patent Publication No. Sho 49-4530, Japanese Patent Application Laid-Open (Kokai) No. Sho 50-5683 or Japanese Patent Application Laid-Open (Kokai) No. Sho 54-149731; which is known as C.I. 48010, C.I. 48015 (Basic Red 13), C.I. 48020 (Basic Violet 7), C.I. 48030 (Basic Violet 21), C.I. 48035 (Basic Orange 21), C.I. 48040 (Basic Orange 22), C.I. 48055 (Basic Yellow 11), C.I. 48060 (Basic Yellow 21), C.I. 48065 (Basic Yellow 12), C.I. 48100 (Basic Yellow 23), C.I. 48016 (Basic Red 14) or C.I. 48056(Basic Yellow 13); or which is described in "Liebigs Ann. Chem. 107–121(1981)" can dye the hair with high dyeing power without causing decomposition of the dye upon hair dying, exhibits excellent light resistance, washing resistance, perspiration resistance, friction resistance and weather resistance, and causes a smaller change in color tone of the dye after storage as compared with that rightly after preparation because the dye exists in the composition stably.

In one aspect of the present invention, there is thus provided a hair dye composition comprising, as a direct dye, a compound represented by the following formula (1):

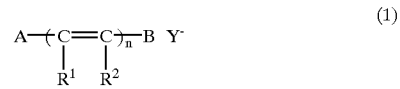

[wherein, $R^1$ and $R^2$ each independently represents a hydrogen atom or a $C_{1-6}$ alkyl group which may have a substituent, A represent a group of the following formula (2):

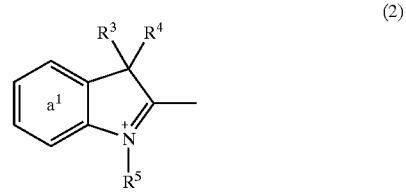

(in which, $R^3$, $R^4$ and $R^5$ each independently represents a $C_{1-6}$ alkyl group which may have a substituent, or $R^4$ and $R^1$ may be coupled together to form a cyclic structure, and benzene ring $a^1$ may have a substituent other than a sulfonic acid group or may be condensed with an aromatic ring), or a group of the following formula (3):

(in which, W represents an aralkyl group, a carbamoylalkyl group or a group —T—$NR^6R^7$ (in which $R^6$ and $R^7$ each independently represents a $C_{1-6}$ alkyl group which may have a substituent, an aromatic group which may have a substituent or a heterocyclic group which may have a substituent, or $R^6$ and $R^7$ may form a heterocyclic ring together with the adjacent nitrogen atom, and T represents a divalent linear $C_{1-4}$ hydrocarbon group which may have a substituent), and pyridine ring $a^2$ may be condensed with an aromatic ring), B represents a group represented by the formula —$Z^1$, —$NR^8$—$Z^1$ or —CH=$Z^2$ (in which $Z^1$ represents an aromatic or heterocyclic aromatic group which may have a substituent, $R^8$ represents a hydrogen atom, a $C_{1-4}$ alkyl group which may have a substituent or an aromatic group which may have a substituent or $R^8$ and $Z^1$ may be coupled together to form a nitrogen-containing heterocyclic group which may have a substituent, and $Z^2$ represents a divalent group obtained by removing two hydrogen atoms from the methylene group on the ring of a heterocyclic aromatic compound which may have a substituent, with the proviso that when A is a group of the formula (2), B represents the group $-Z^1$, and $Z^1$ represents an aromatic group or, when A is a group of the formula (2), B represents the group $-CH=Z^2$, $Z^2$ represents an indolinidene group and n does not stand for 0, the aromatic or indolinidene group has at least one substituent represented by the formula: $-NR^9R^{10}$ (in which $R^9$ represents a $C_{1-4}$ alkyl group having as a substituent a chlorine atom or a cyano, acylamino, alkoxy, monoalkylamino, dialkylamino or trimethylammoniumyl group, or a phenyl group which may have a substituent and $R^{10}$ represents a $C_{1-6}$ alkyl group which may have a substituent), n stands for an integer of 1 to 3 when B represents the group $-Z^1$ or group $-NR^8-Z^1$ and n stands for an integer of 0 to 3 when B represents the group $-CH=Z^2$; and $Y^{31}$ represents an anion.

amino group which may be substituted with one or two $C_{1-6}$ alkyl groups which may be substituted with a hydroxyl group, nitro group, hydroxyl group, and $C_{1-6}$ acyl groups. This $a^1$ may be cyclocondensed with an aromatic ring and a naphthalene ring may be mentioned as such a condensed ring.

In the formula (1), when A is the group (3), examples of the aralkyl group represented by W include benzyl, 1-phenethyl and 2-phenethyl groups, while those of the carbamoylalkyl group include carbamoylethyl.

In the formula (1), when A is the group (3) and W is the group $-T-NR^6R^7$, examples of the $C_{1-6}$ alkyl group represented by $R^6$ or $R^7$ include methyl, ethyl, propyl, butyl, pentyl, hexyl, isopropyl, isobutyl and isopentyl groups, those of the aromatic group include phenyl and naphthyl, and those of the heterocyclic group include imidazolyl and triazolyl. $R^6$ and $R^7$ may be the same or different, or the group $-NR^6R^7$ may be quaternized. In this group, $R^6$ and $R^7$ may form a heterocyclic ring, together with the adjacent nitrogen atom. As such a heterocyclic ring, pyrrolidine, piperidine, morpholine, piperazine, imidazole, triazole and pyridinium rings may be mentioned by way of example. $R^6$ or $R^7$ may have a substituent such as phenyl group, cyano group, chlorine atom, hydroxyl group, amino group, methoxy group, diethylamino group or a group of the following formula:

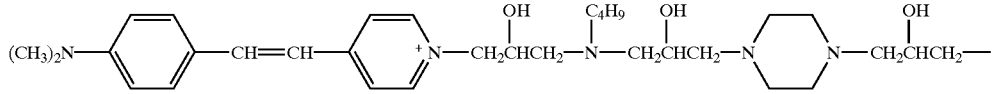

BEST MODE FOR CARRYING OUT THE INVENTION

In the formula (1), examples of the $C_{1-6}$ alkyl group represented by $R^1$ or $R^2$ include methyl, ethyl, propyl, butyl, pentyl, hexyl, isopropyl, isobutyl and isopentyl groups. $R^1$ and $R^2$ may be the same or different. Examples of the substituent which may be possessed by them include cyano group, chlorine atom, hydroxyl group, amino group, methoxy group and diethylamino group. When B stands for the group $-Z^1$ or $-NR^8-Z^1$, particularly preferred as n is 1, while when B stands for the group $-CH=Z^2$, 0 or 1 is particularly preferred. When B stands for the group $-CH=Z^2$, 0 is most preferred as n because of stability to an oxidizing agent, particularly to hydrogen peroxide.

In the formula (1), when A represents a group of the formula (2), examples of the $C_{1-6}$ alkyl group represented by $R^3$, $R^4$ or $R^5$ include methyl ethyl, propyl, butyl, pentyl, hexyl, isopropyl, isobutyl and isopentyl groups. $R^3$, $R^4$ and $R^5$ may be the same or different. $R^4$ and $R^1$ may form a cyclic structure together with two adjacent carbon atoms and as such a cyclic structure, 5— to 7-membered ones are preferred. $R^3$, $R^4$ or $R^5$ may have, as a substituent, a sulfonic acid group or salt thereof, cyano group, chlorine atom, hydroxyl group, amino group, alkoxy group, monoalkylamino group, dialkylamino group, trimethylammoniumyl group, oxo group, carbamoyl group, carboxy group or aryl group.

Examples of the substituent which may be possessed by benzene ring $a^1$ in the formula (2) include $C_{1-6}$ alkyl groups which may be substituted with a hydroxyl group, $C_{1-6}$ alkoxy groups, halogen atoms, $C_{2-7}$ alkoxycarbonyl groups, carboxy group or salts thereof, $C_{1-6}$ acylamino groups, In the formula (3), the divalent linear $C_{1-4}$ hydrocarbon group represented by T is, for example, a methylene, ethylene, trimethylene, tetramethylene or propylene group, with the ethylene or trimethylene group being particularly preferred. T may have, for example, a methyl, ethyl, phenyl, benzyl or hydroxyl group as a substituent.

In the formula (3), pyridine ring $a^2$ may be substituted with an aromatic ring and examples of such a condensed heterocyclic ring include quinoline and isoquinoline rings.

In the formula (1), as a group represented by A, groups of the formula (2) are preferred because of stability to an oxidizing agent, particularly to hydrogen peroxide.

In the formula (1), B represents the group $-Z^1$, $-NR^8-Z^1$ or $-CH=Z^2$. Examples of $-Z^1$ include groups of the following formulas:

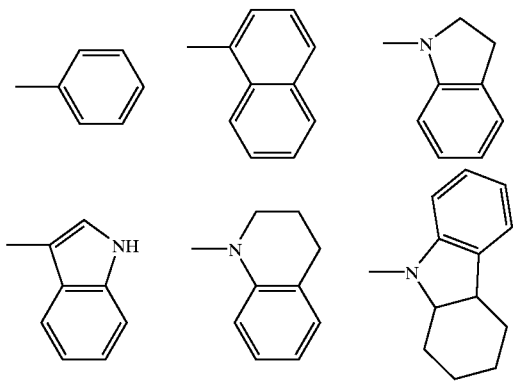

-continued

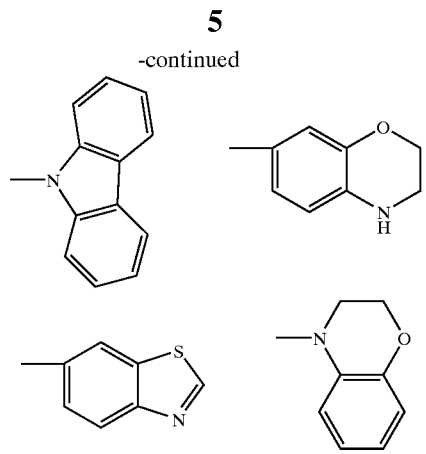

These Z¹ may have, as a substituent, halogen atom, hydroxyl group, cyano group, $C_{1-8}$ alkyl group which may have a substituent, $C_{1-8}$ alkoxy group which may have a substituent, amino group which may have a substituent, phenyl group which may have a substituent or a group of the formula: A—CH=CH—Z¹—D— (in which A and Z¹ have the same meanings as described above and D represents a group —NHCONH— or —NHCO—D'—CONH— (in which D' represents an alkylene, phenylene or naphthylene group)). When Z¹ represents an aromatic group, it contains at least one —NR⁹R¹⁰.

Examples of the substituent for the alkyl or alkoxyl group which may be substituted for Z¹ include cyano group, chlorine atom, dialkylamino group and trialkylammmoniumyl group. Examples of the substituent for the amino group which may be substituted for Z¹ include alkyl and aryl groups. These substituents may be substituted, for example, with an aryl group, an alkoxy group, an alkyl group, a chlorine atom, a cyano group, an amino group, a monoalkylamino group, a dialkylamino group or a trialkylammoniumyl group.

As —Z¹, preferred are the following groups:

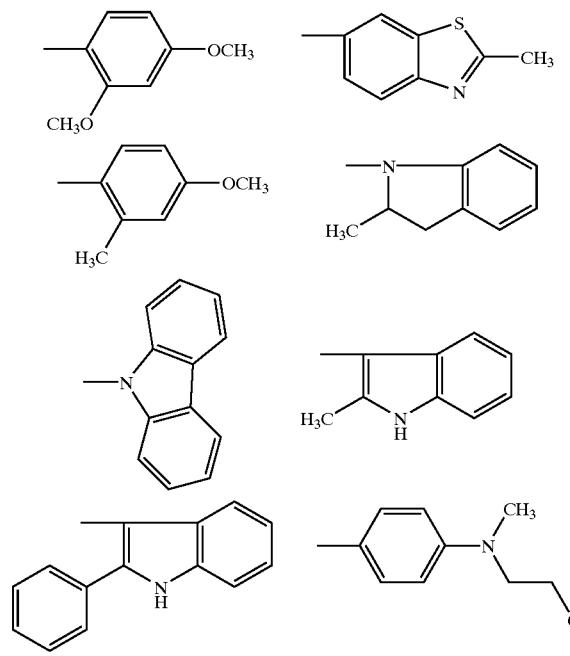

-continued

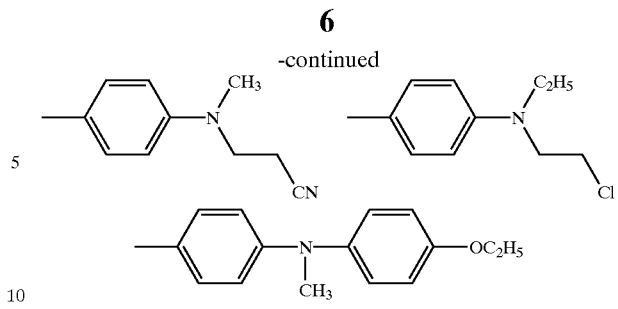

$R^8$ is, for example, a hydrogen atom or a methyl, ethyl, propyl, butyl, phenyl, 4-hydroxyphenyl or 4-methoxyphenyl group.

As —CH=Z², following groups represented by the formula (5) or (6) can be mentioned by way of example:

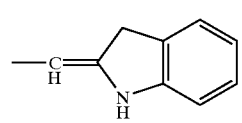
(5)

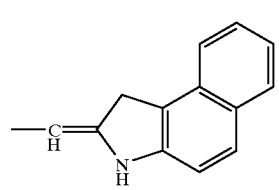
(6)

As a substituent which may be possessed by Z², $C_{1-6}$ alkyl groups and the like can be mentioned. These alkyl groups may have a substituent similar to that exemplified as the substituent which may be possessed by $R^3$, $R^4$ or $R^5$. When Z² represents an indolinidene group and n does not stand for 0, the indolinidene group have at least one group —NR⁹R¹⁰.

Among the compounds represented by the formula (1), preferred for stability to an oxidizing agent, particularly to hydrogen peroxide are those wherein when A is represented by the formula (2), B is represented by a group of the formula —CH=Z², and n stands for 0, the group of the formula —CH=Z² is a group substituted, at a specific position of the formula (5) or (6), by an alkyl group, that is a group of the following formula (7):

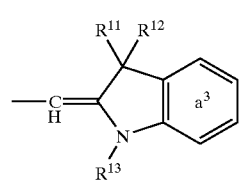
(7)

[wherein, $R^{11}$, $R^{12}$ and $R^{13}$ each independently represents a $C_{1-6}$ alkyl group which may have a substituent, and a benzene ring $a^3$ may have a substituent other than a sulfonic acid group or may be cyclocondensed with an aromatic ring].

In short, compounds having a group of the formula (2) as A, a group of the formula (7) as B and 0 as n are most preferred for stability to an oxidizing agent, particularly to hydrogen peroxide. Such compounds (1) have the following formula (4):

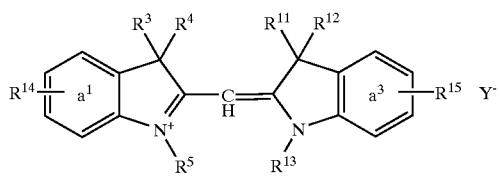

(4)

[wherein, $R^3$, $R^4$, $R^5$, $R^{11}$, $R^{12}$ and $R^{13}$ each independently represents a $C_{1-6}$ alkyl group which may have a substituent; $R^{14}$ and $R^{15}$ each independently represents a hydrogen atom, a $C_{1-6}$ alkyl group which may be substituted by a hydroxyl group, a $C_{1-6}$ alkoxy group, a halogen atom, a $C_{2-7}$ alkoxycarbonyl group, a carboxy group or salt thereof, a $C_{1-6}$ acylamino group, an amino group which may be substituted with one or two $C_{1-6}$ alkyl groups which may be substituted by a hydroxyl group, a nitro group, a hydroxyl group or a $C_{1-6}$ acyl group; benzene rings $a^1$ and $a^3$ may each be cyclocondensed with an aromatic ring; and Y represents an anion].

In the formula (4), examples of the $C_{1-6}$ alkyl group represented by $R^3$, $R^4$, $R^5$, $R^{11}$, $R^{12}$ or $R^{13}$ include methyl, ethyl, propyl, butyl, pentyl, hexyl, isopropyl, isobutyl and isopentyl groups. $R^3$, $R^4$, $R^5$, $R^{11}$, $R^{12}$ and $R^{13}$ may be the same or different. Examples of the substituent which $R^3$, $R^4$, $R^5$, $R^{11}$, $R^{12}$ or $R^{13}$ may have include sulfonic acid group or salts thereof, cyano group, chlorine atom, hydroxyl group, amino group, alkoxy groups, monoalkylamino groups, dialkylamino groups, trimethylammoniumyl group, oxo group, carbamoyl group, carboxy group and aryl groups.

As $R^{14}$ or $R^{15}$, examples of the $C_{1-6}$ alkyl group which may be substituted by a hydroxyl group include, in addition to the above-exemplified $C_{1-6}$ alkyl groups, hydroxymethyl, 1-hydroxyethyl, 2-hydroxyethyl, 1-hydroxypropyl and 3-hydroxypropyl groups. Examples of the $C_{1-6}$ alkoxy group represented by $R^{14}$ or $R^{15}$ include methoxy, ethoxy, propoxy, butoxy, pentyloxy, hexyloxy, isopropoxy, isobutoxy and isopentyloxy groups. Examples of the halogen atom represented by $R^{14}$ or $R^{15}$ include fluorine, chlorine, bromine and iodine atoms. Examples of the $C_{2-7}$ alkoxycarbonyl group represented by $R^{14}$ or $R^{15}$ include methoxycarbonyl, ethoxycarbonyl, propoxycarbonyl, butoxycarbonyl, pentyloxycarbonyl, hexyloxycarbonyl, isopropoxycarbonyl, isobutoxycarbonyl and isopentyloxycarbonyl groups. Examples of the salt of a carboxy group represented by $R^{14}$ or $R^{15}$ include ammonium salts, lithium salts, sodium salts and potassium salts. Examples of the $C_{1-6}$ acylamino group represented by $R^{14}$ or $R^{15}$ include formamido, acetamido, propionamido, butanoylamino, pentanoylamino, hexanoylamino, isopropionamido, isobutanoylamino and isopentanoylamino groups. Examples of the amino group which may be substituted by one or two $C_{1-6}$ alkyl groups which may be substituted by a hydroxyl group include amino, monomethylamino, dimethylamino, monoethylamino, diethylamino, monopropylamino, dipropylamino, mono(2-hydroxyethylamino, bis(2-hydroxyethyl)amino, mono(3-hydroxypropyl)amino, bis(3-hydroxypropyl)amino, mono(2-hydroxypropyl)amino, and bis(2-hydroxypropyl)amino groups. Examples of the $C_{1-6}$ acyl group represented by $R^{14}$ or $R^{15}$ include formyl, acetyl, propanoyl, butanoyl, pentanoyl, hexanoyl, isopropanoyl, isobutanoyl and isopentanoyl groups.

In the formula (4), the benzene rings $a^1$ and $a^3$ may each be cyclocondensed with an aromatic ring and as such a condensed ring, a naphthalene ring may be mentioned as an example.

In the formulas (1) and (4), examples of the anion represented by $Y^-$ include chloride ions, bromide ions, iodide ions, trichlorozincic acid ions, tetrachlorozincic acid ions, sulfuric acid ions, hydrogensulfate ions, methyl sulfate ions, phosphoric acid ions, formic acid ions, acetic acid ions, perchloric acid ions and tetrafluoroboric acid ions.

The following are specific examples of the direct dye (1) to be used in the present invention:

Compounds having a group of the formula (2) as A:

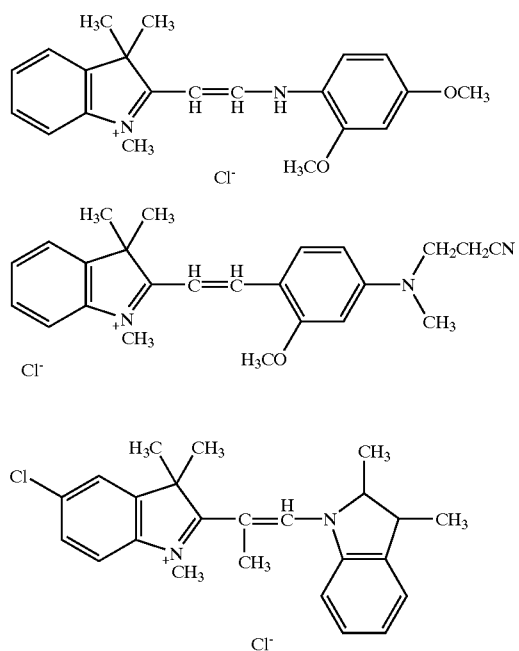

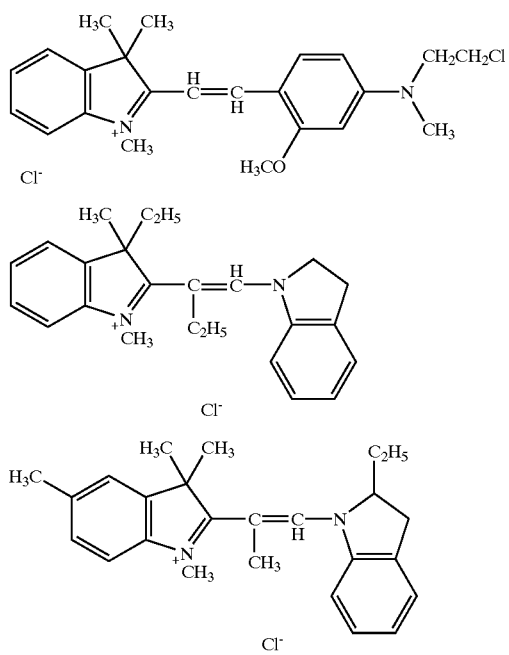

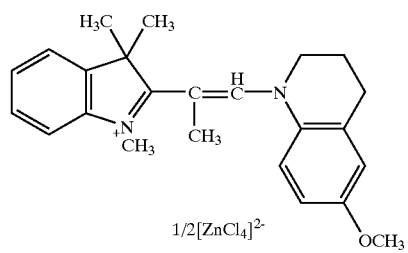
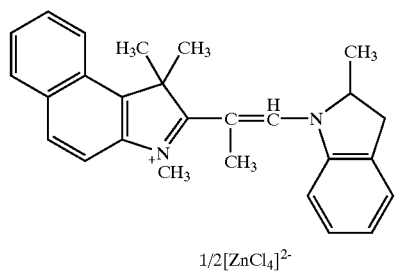
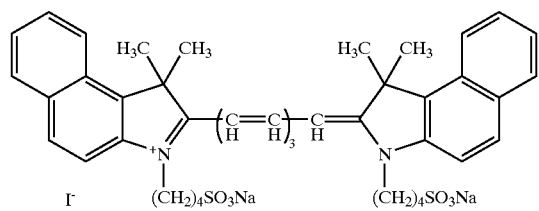
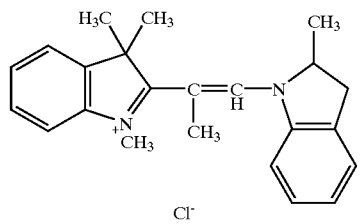
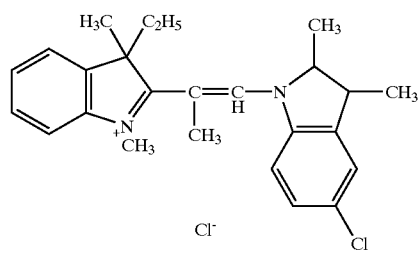
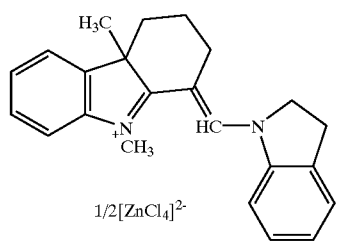
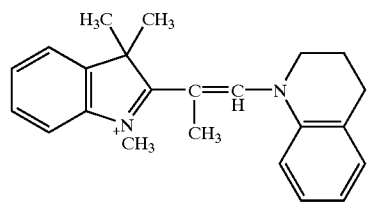
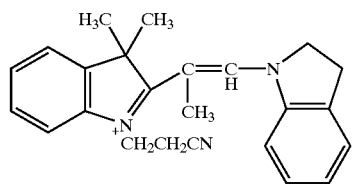
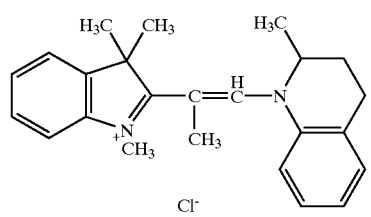
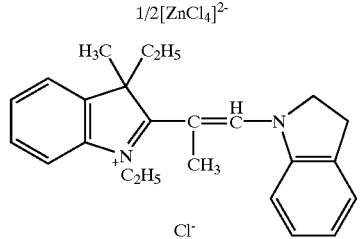
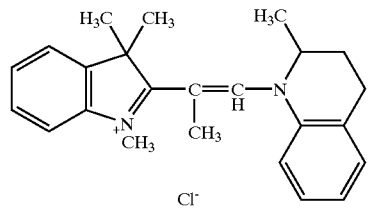
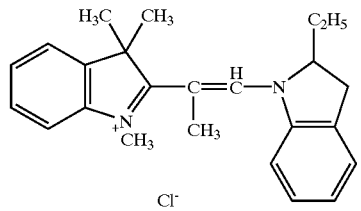
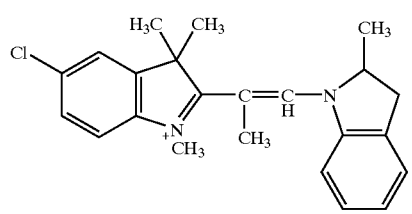
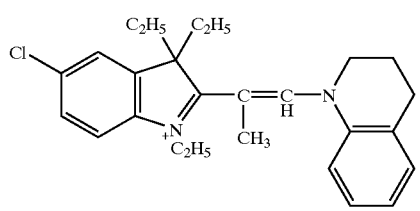

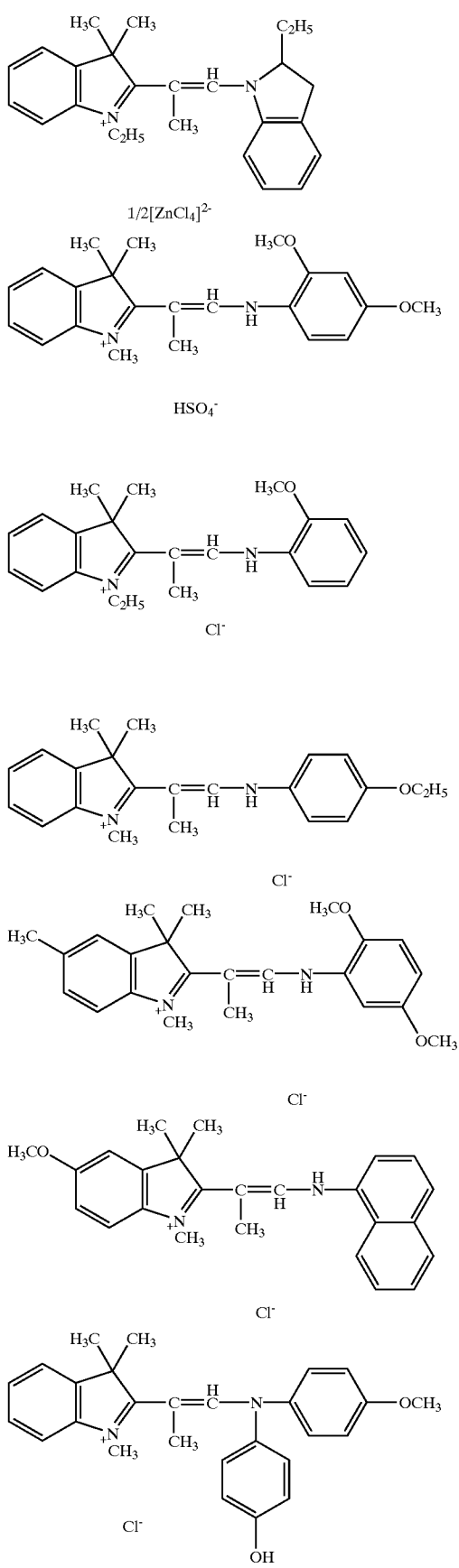
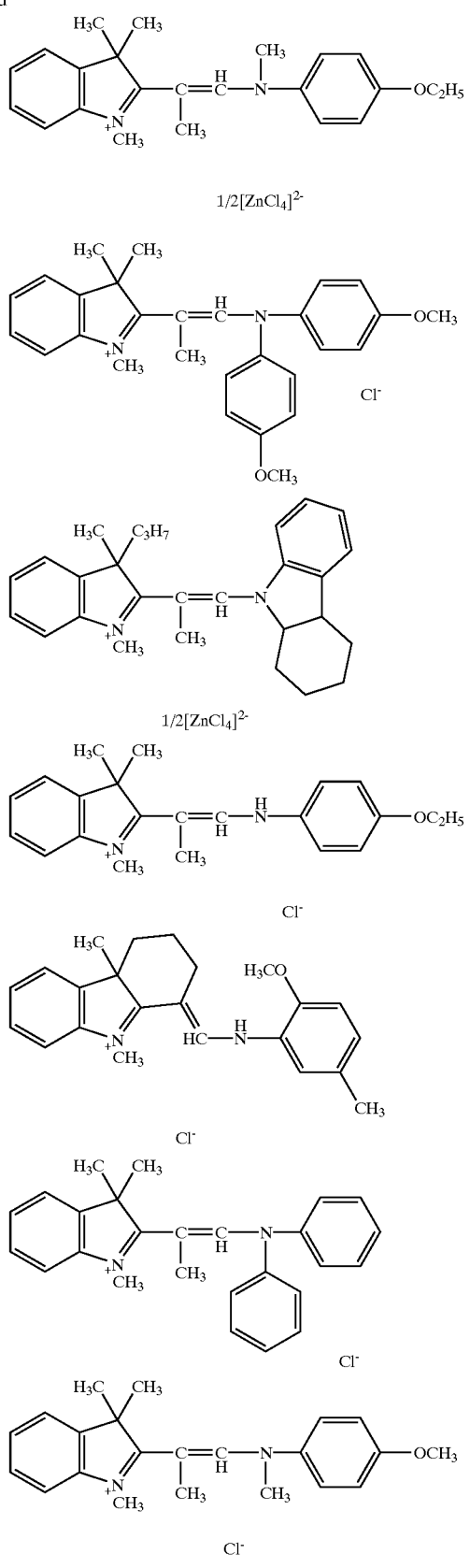

-continued
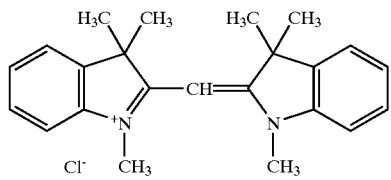
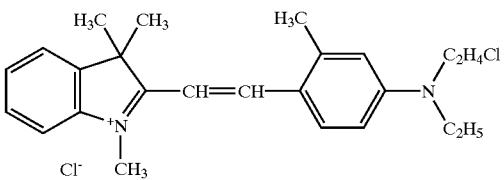
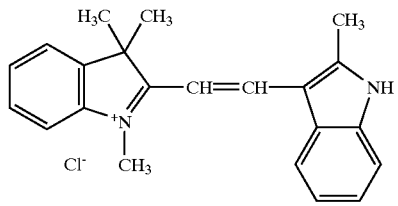
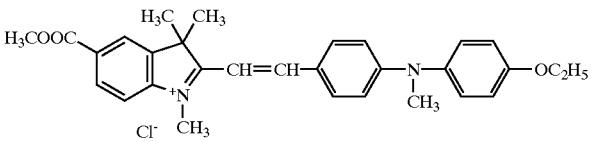
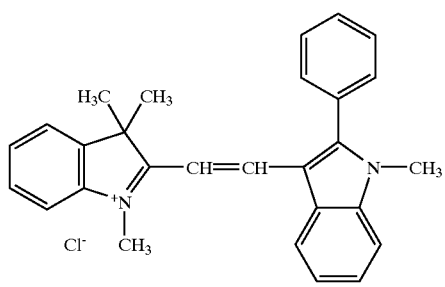
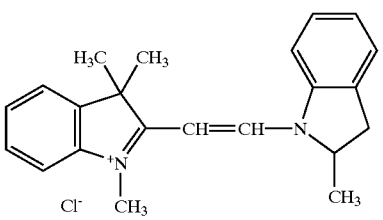
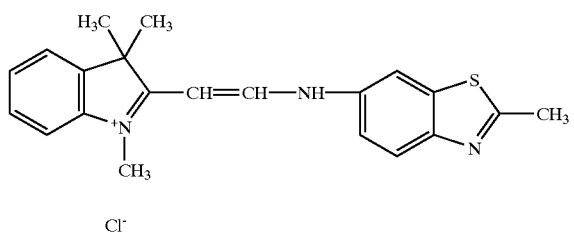
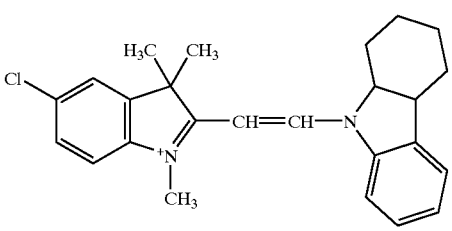
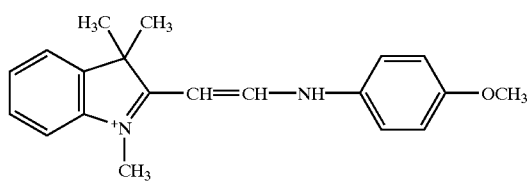
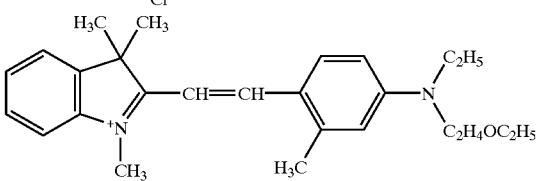
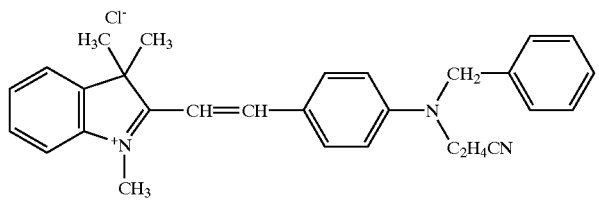
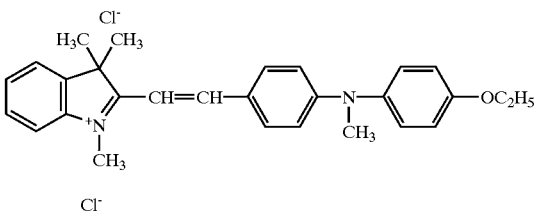
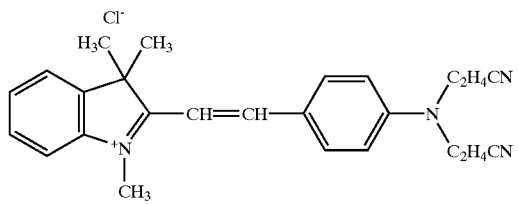
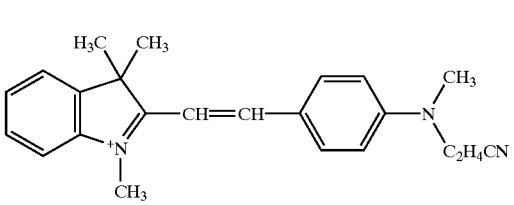

-continued
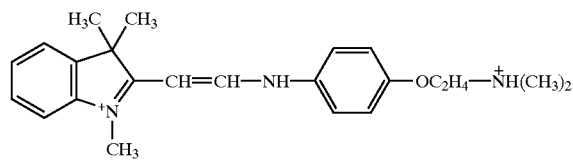
[ZnCl₄]²⁻
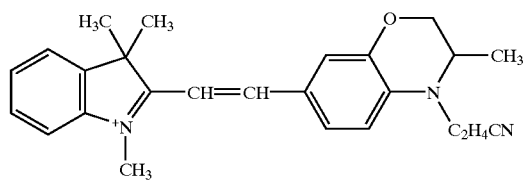
1/2[ZnCl₄]²⁻
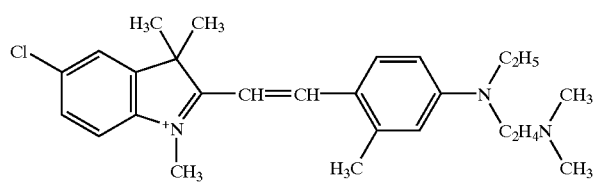
1/2[ZnCl₄]²⁻
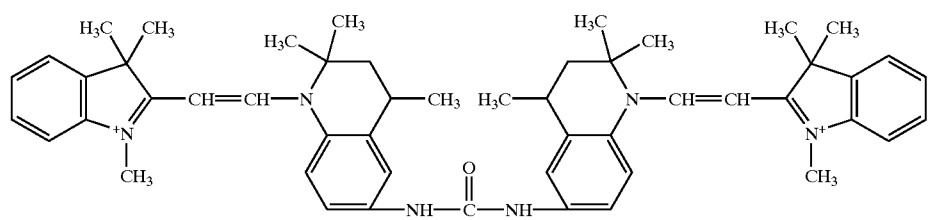
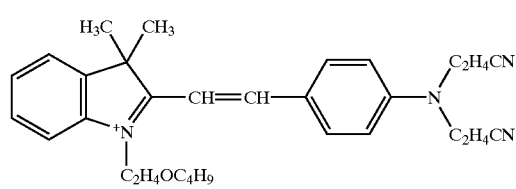
Cl⁻
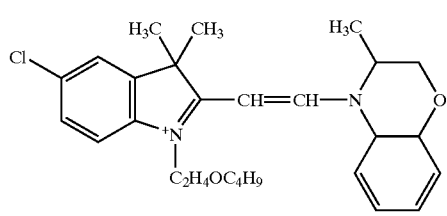
Cl⁻
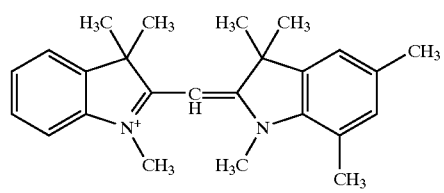
ClO₄⁻
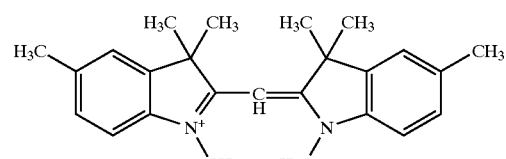
BF₄⁻
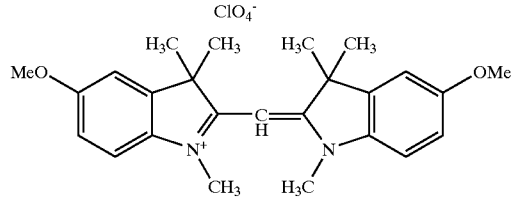
BF₄⁻
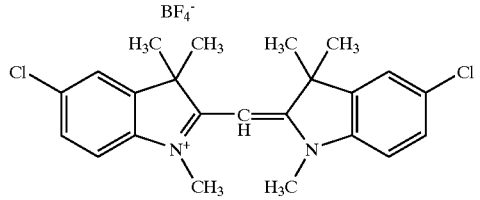
BF₄⁻
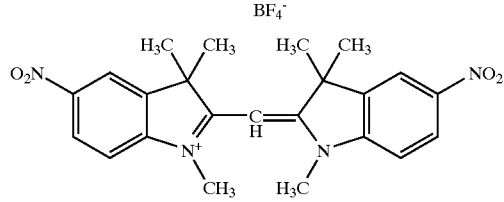
BF₄⁻
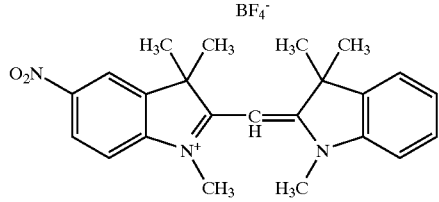
BF₄⁻

-continued
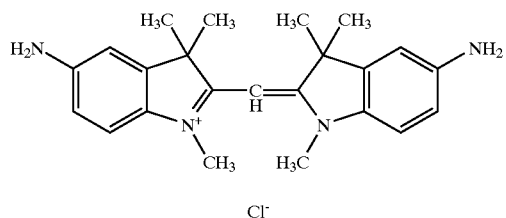
Cl⁻
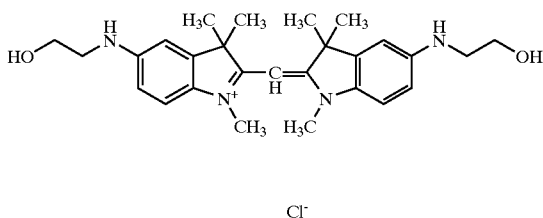
Cl⁻
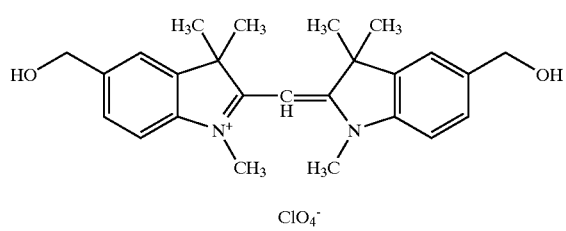
ClO₄⁻
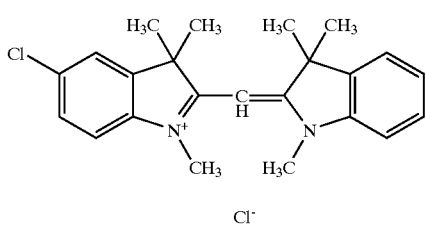
Cl⁻
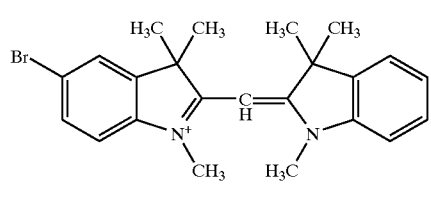
Br⁻
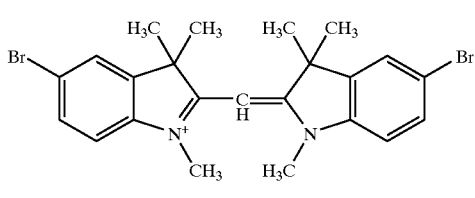
Br⁻
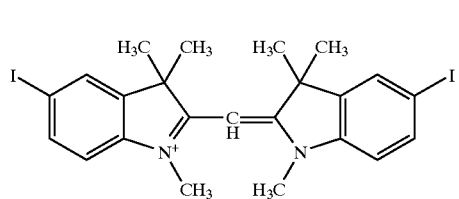
I⁻
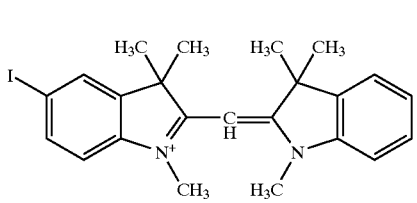
I⁻
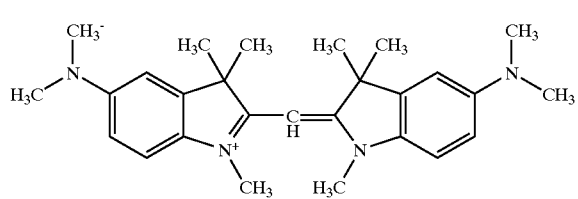
I⁻
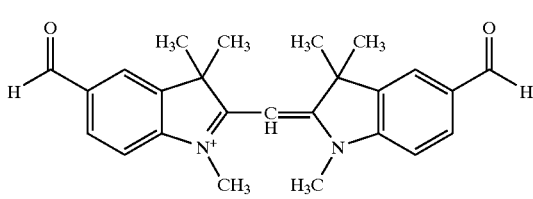
Cl⁻
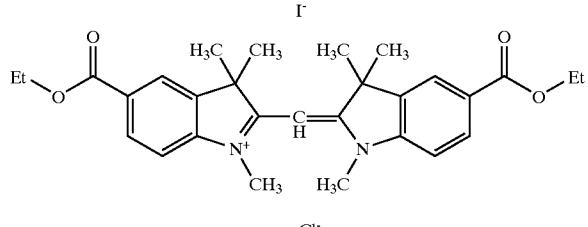
Cl⁻
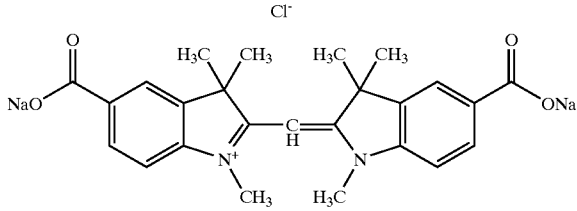
Cl⁻
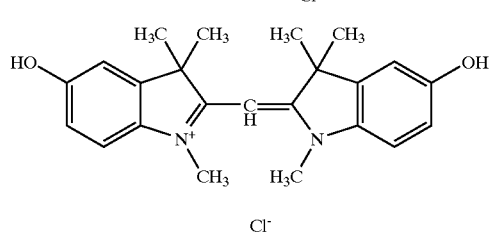
Cl⁻
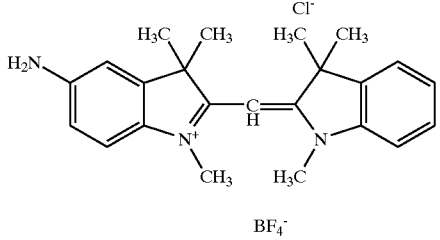
BF₄⁻

-continued
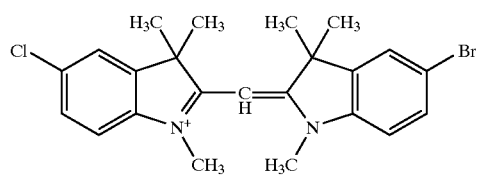
Cl⁻
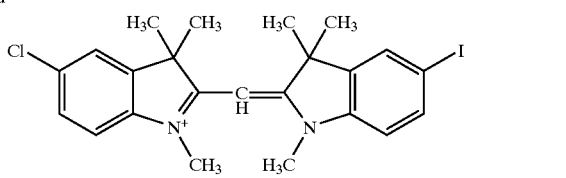
Cl⁻
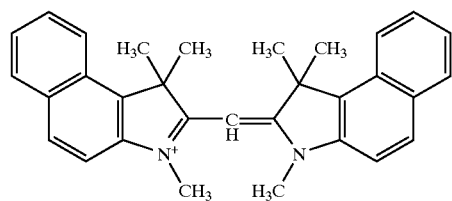
Cl⁻
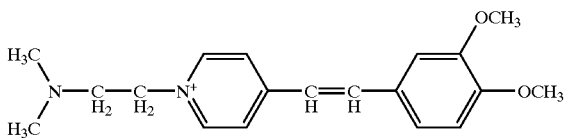
Cl⁻
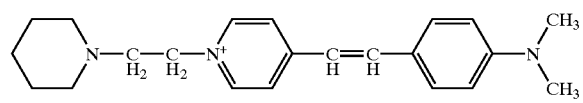
Cl⁻
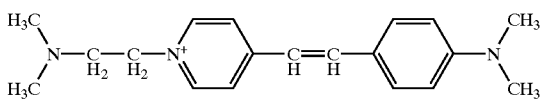
Cl⁻
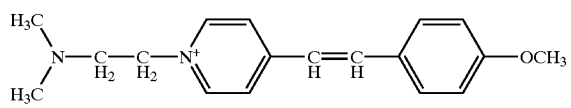
Cl⁻
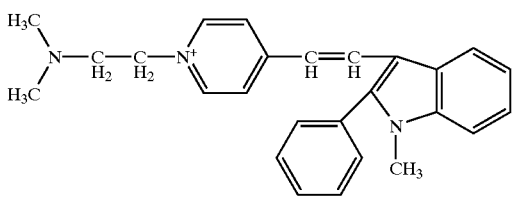
Cl⁻
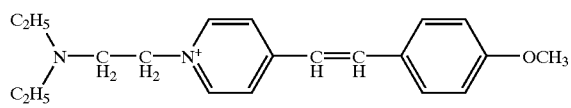
Cl⁻
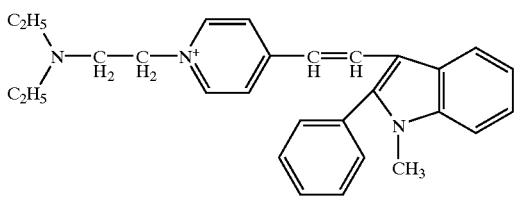
Cl⁻
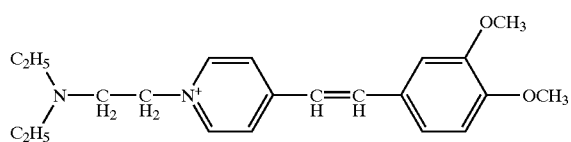
Cl⁻
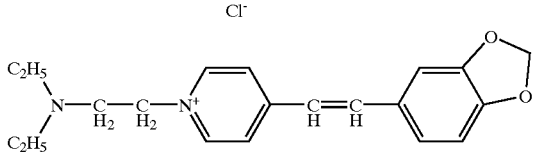
Cl⁻
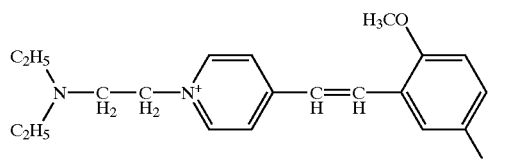
Cl⁻
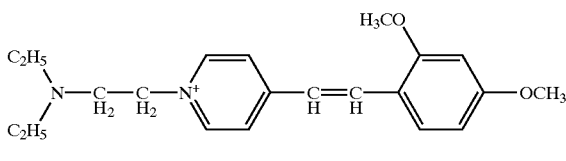
Cl⁻
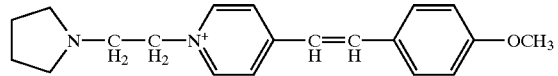
Cl⁻
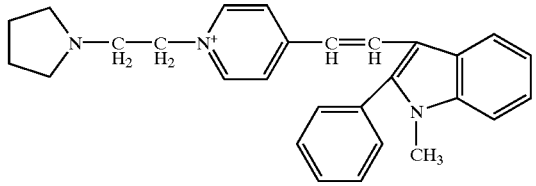
Cl⁻

-continued
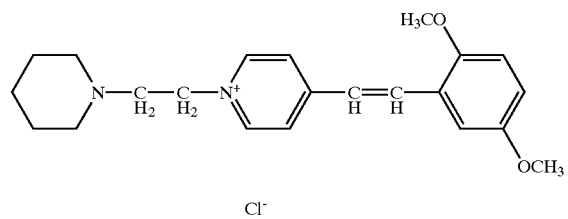
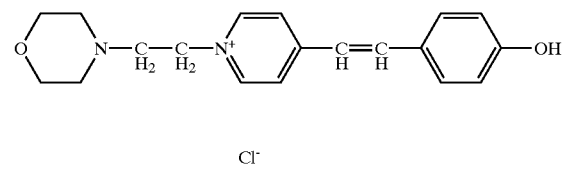
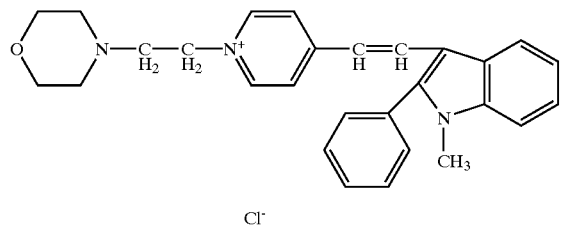
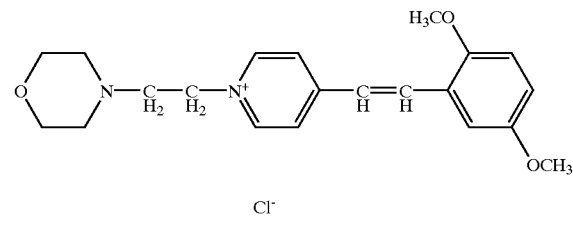
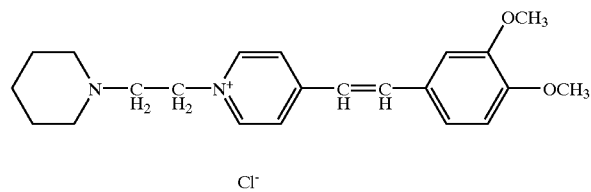
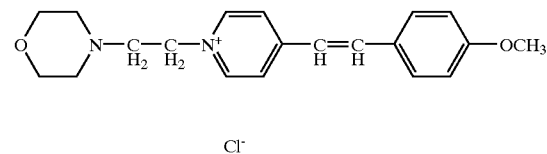
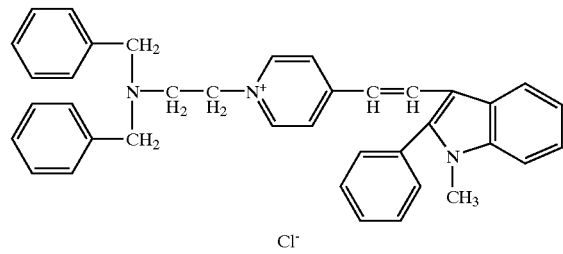
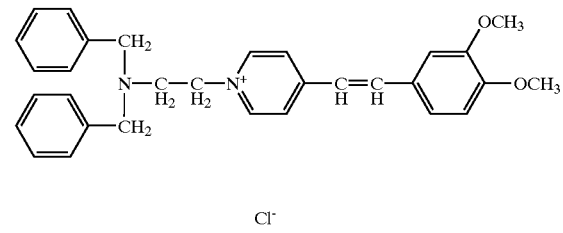
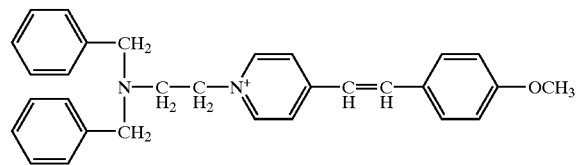
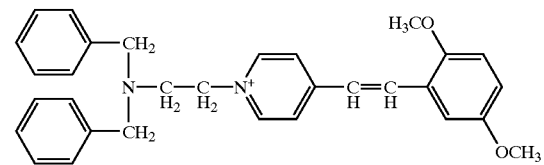
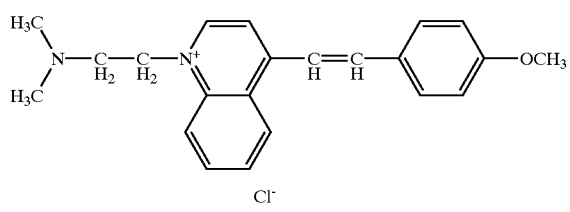
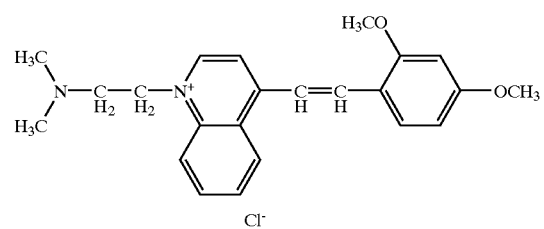

-continued

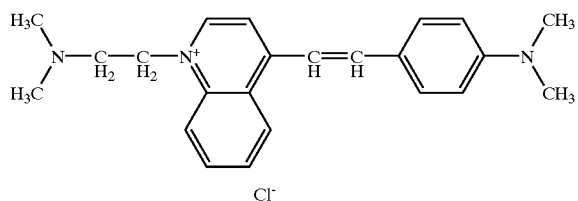

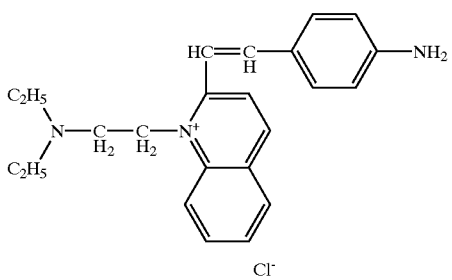

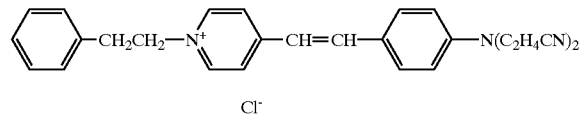

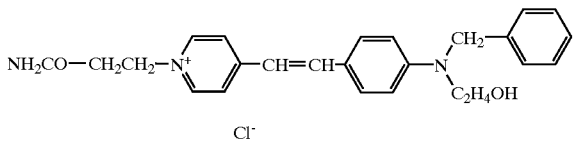

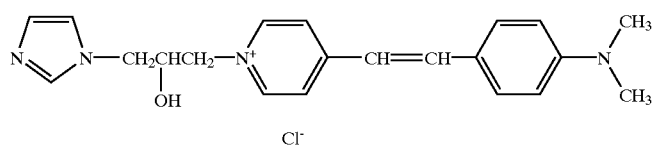

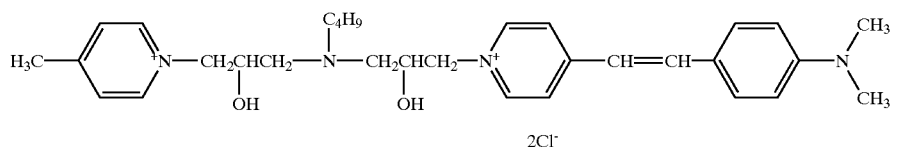

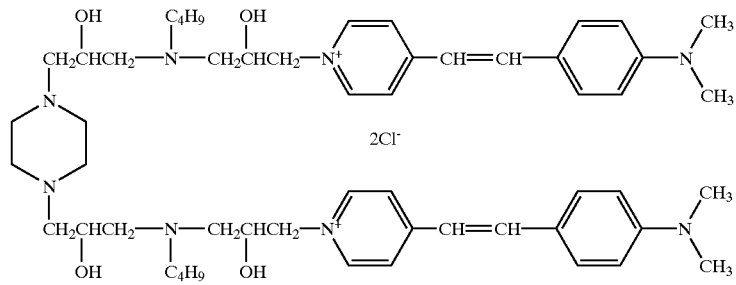

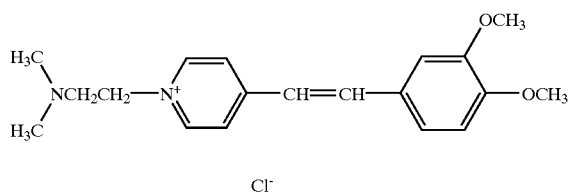

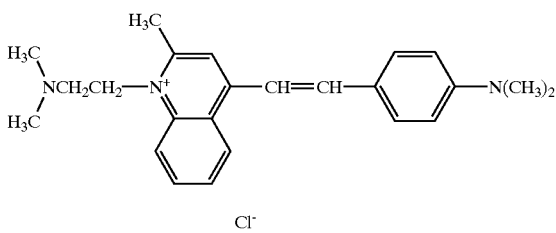

Among the direct dyes (1), those represented by the formula (4) can be prepared, for example, by the method described in "THE CHEMISTRY OF HETEROCYCLIC COMPOUNDS —THE CYANINE DYES AND RELATED COMPOUNDS—, 54–55(1964)" or "Liebigs Ann. Chem., 107–121(1981)".

As the direct dye (1), one or more of the above-exemplified compounds may be used. Alternatively, another direct dye can be used in combination.

Examples of the direct dye other than the direct dye (1) include Basic Blue 7 (C.I. 42595), Basic Blue 26 (C.I. 44045), Basic Blue 99 (C.I. 56059), Basic Violet 10 (C.I. 45170), Basic Violet 14 (C.I. 42515), Basic Brown 16 (C.I. 12250), Basic Brown 17 (C.I. 12251), Basic Red 2 (C.I. 50240), Basic Red 22 (C.I. 11055), Basic Red 76 (C.I. 12245), Basic Red 118 (C.I. 12251:1) and Basic Yellow 57(C.I. 12719); and basic dyes as described in Japanese Patent Publication No. Sho 58-2204, Japanese Patent Application Laid-Open No. Hei 9-118832, Japanese Language Laid-Open Publication (PCT) No. Hei 8-501322 or Japanese Language Laid-Open Publication (PCT) No. Hei 8-507545.

The direct dye (1) is preferably added in an amount of 0.01 to 20 wt. %, more preferably 0.05 to 10 wt. %, especially 0.1 to 5 wt. % on the basis of the entirety of the composition (after mixing of all the parts when a two-part or three-part composition is employed; this will apply equally hereinafter). When another direct dye is used in combination, the content of it with the direct dye (1) preferably ranges from 0.05 to 10 wt. %, especially 0.1 to 5 wt. % based on the whole composition.

The hair dye composition of the present invention is preferably adjusted to pH 6 to 11, with pH 8 to 11 being more preferred. Examples of the alkali agent to be used for pH adjustment include ordinarily employed ones such as ammonia, organic amines and salts thereof. The alkali agent is preferably added in an amount of 0.01 to 20 wt. %, more preferably 0.1 to 10 wt. %, especially 0.5 to 5 wt. %.

In the hair dye composition of the present invention, an oxidizing agent can be incorporated. In this case, hair dyeing and bleaching can be carried out simultaneously, which facilitates more vivid hair dyeing. Ordinarily employed oxidizing agents, for example, hydrogen peroxide, persulfates such as ammonium persulfate, potassium persulfate and sodium persulfate; perborates such as sodium perborate, percarbonates such as sodium percarbonate and bromates such as sodium bromate and potassium bromate are usable. Out of them, hydrogen peroxide is especially preferred. The oxidizing agent is added in an amount of 0.5 to 10 wt. %, especially 1 to 8 wt. %, on the basis of the entirety of the composition.

In the hair dye composition of the present invention, an oxidation dye can be incorporated further. This incorporation enables remarkable vivid dyeing not attainable by the single use of an oxidation dye. As the oxidizing agent, the above-exemplified ones can be used, with hydrogen peroxide being particularly preferred. Alternatively, an oxidizing enzyme such as laccase can be employed. For the oxidation dye, known developers and couplers ordinarily employed for an oxidation type hair dye can be used.

Examples of the developer include p-phenylenediamines having one or several groups selected from $NH_2$—, NHR— and $NR_2$— groups (R represents a $C_{1-4}$ alkyl or hydroxyalkyl group) such as p-phenylenediamine, p-toluylenediamine, N-methyl-p-phenylenediamine, chloro-p-phenylenediamine, 2-(2'-hydroxyethylamino)-5-aminotoluene, N,N-bis-(2-hydroxyethyl)-p-phenylenediamine, 2-hydroxyethyl-p-phenylenediamine, 2,6-dimethyl-p-phenylenediamine, methoxy-p-phenylenediamine, 2,6-dichloro-p-phenylenediamine, 2-chloro-6-methyl-p-phenylenediamine, 6-methoxy-3-methyl-p-phenylenediamine, 2,5-diaminoanisole, N-(2-hydroxypropyl)-p-phenylenediamine and N-2-methoxyethyl-p-phenylenediamine; 2,5-diaminopyridine derivatives and 4,5-diaminopyrazole derivatives; p-aminophenols such as p-aminophenol, 2-methyl-4-aminophenol, N-methyl-p-aminophenol, 3-methyl-4-aminophenol, 2,6-dimethyl-4-aminophenol, 3,5-dimethyl-4-aminophenol, 2,3-dimethyl-4-aminophenol and 2,5-dimethyl-4-aminophenol; o-aminophenols, o-phenylenediamines, 4,4'-diaminophenylamine and hydroxypropylbis(N-hydroxyethyl-p-phenylenediamine); and salts thereof.

Examples of the coupler include 1-naphthol, 1,5-dihydroxynaphthalene, 1,7-dihydroxynaphthalene, 2,7-dihydroxynaphthalene, 5-amino-2-methylphenol, 5-(2'-hydroxyethylamino)-2-methylphenol, 2,4-diaminoanisole, m-toluylenediamine, resorcin, m-phenylenediamine, m-aminophenol, 4-chlororesorcin, 2-methylresorcin, 2,4-diaminophenoxyethanol, 2,6-diaminopyridine, 2-amino-3-hydroxypyridine, 4-hydroxyindole, 6-hydroxyindole, 2,4-diamino-6-hydroxypyrimidine, 2,4,6-triaminopyrimidine, 2-amino-4,6-dihydroxypyrimidine, 4-amino-2,6-dihydroxypyrimidine, 4,6-diamino-2-hydroxypyrimidine and 1,3-bis(2,4-diaminophenoxy)propane; and salts thereof.

As a developer or coupler, at least one of the above-exemplified ones can be used. Although no particular limitation is imposed on its content, it is preferably added in an amount of 0.01 to 20 wt. %, especially 0.5 to 10 wt. % based on the whole composition.

To the hair dye composition of the present invention, a known autoxidation dye typified by an indole or an indoline, or a known direct dye such as a nitro dye or a disperse dye can also be added.

When an anionic component (such as anionic surfactant or anionic polymer) is added to the hair dye composition of the present invention, it is preferred to satisfy the following equation:

"Ion activity concentration of an anionic component/ion activity concentration of a cationic direct dye (1)≦8"

The term "ion activity concentration" as used herein means "molar concentration x ionic valence"

Addition of a polyol, polyol alkyl ether, cationic or amphoteric polymer or silicone to the hair dye composition of the present invention is preferred, because the resulting composition can dye the hair uniformly and has improved cosmetic effects.

In addition to the above-described components, those ordinarily employed as a raw material for cosmetics can be added to the hair dye composition of the present invention. Examples of such an optional component include hydrocarbons, animal or vegetable fats and oils, higher fatty acids, organic solvents, penetration promoters, cationic surfactants, natural or synthetic polymers, higher alcohols, ethers, amphoteric surfactants, nonionic surfactants, protein derivatives, amino acids, antiseptics, chelating agents, stabilizing agents, antioxidants, plant extracts, crude drug extracts, vitamins, colorants, perfumes and ultraviolet absorbers.

The hair dye composition of the present invention can be prepared in a conventional manner into a one-part composition, a two-part composition having a first-part component containing an alkali agent and a second-part component containing an oxidizing agent, or a three-part composition having, in addition to these two components, a powdery oxidizing agent such as persulfate. The direct dye (1) can be incorporated in either one or both of these components of the two-part or three-part composition. The one-part type is applied to the hair directly, while the two- or three-part type is applied to the hair after mixing these parts upon hair dyeing.

No particular limitation is imposed on the form of the hair dye composition of the present invention. Examples include powder, transparent liquid, emulsion, cream, gel, paste, aerosol, and aerosol foam. It preferably has a viscosity of 2000 to 100000 mPa·s in the stage of application to the hair (after mixing of all the components when a two-part or three-part type composition is employed).

For dyeing the hair with the hair dye composition of the present invention, it is recommended to apply the hair dye composition of the present invention to the hair at 10 to 50° C. directly when it is one-part type and after mixing when it is two- or three-part type, allow it to act on the hair for 1 to 60 minutes, preferably 3 to 45 minutes, wash the resulting hair and then dry it.

EXAMPLES

Compounds employed in the below-described examples are as follows:

Compound (a)
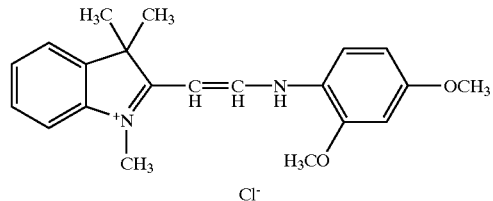

Compound (b)
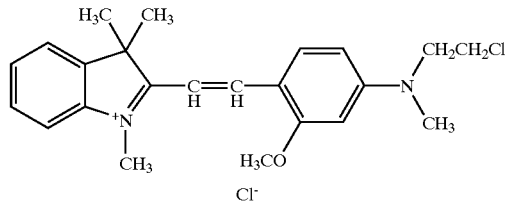

Compound (c)
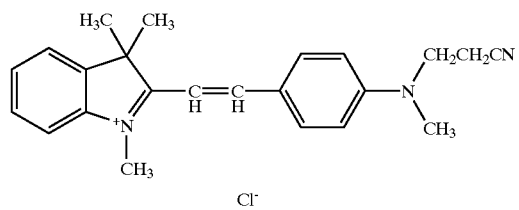

Compound (d)
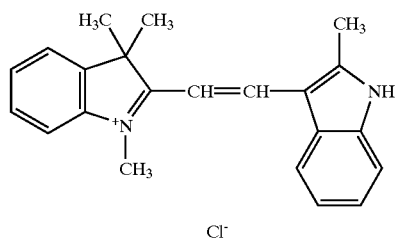

Compound (e)
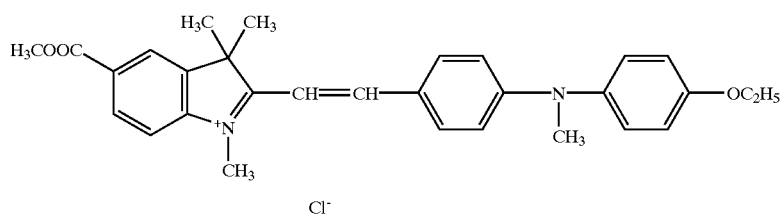

Compound (f)
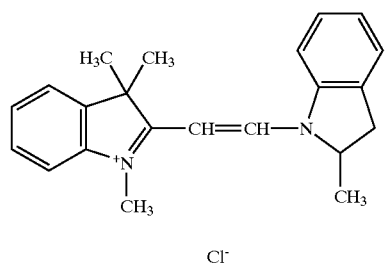

Compound (g)
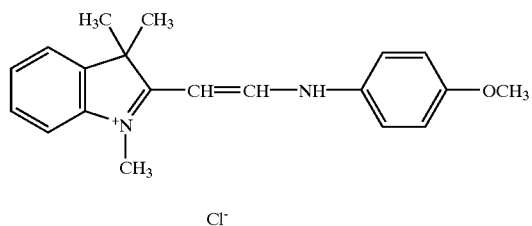

Compound (h)
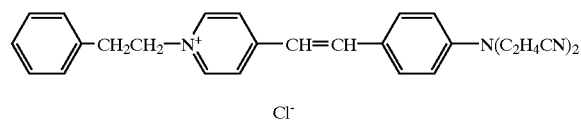

Compound (i)
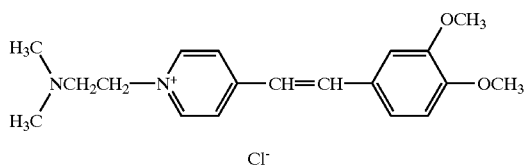

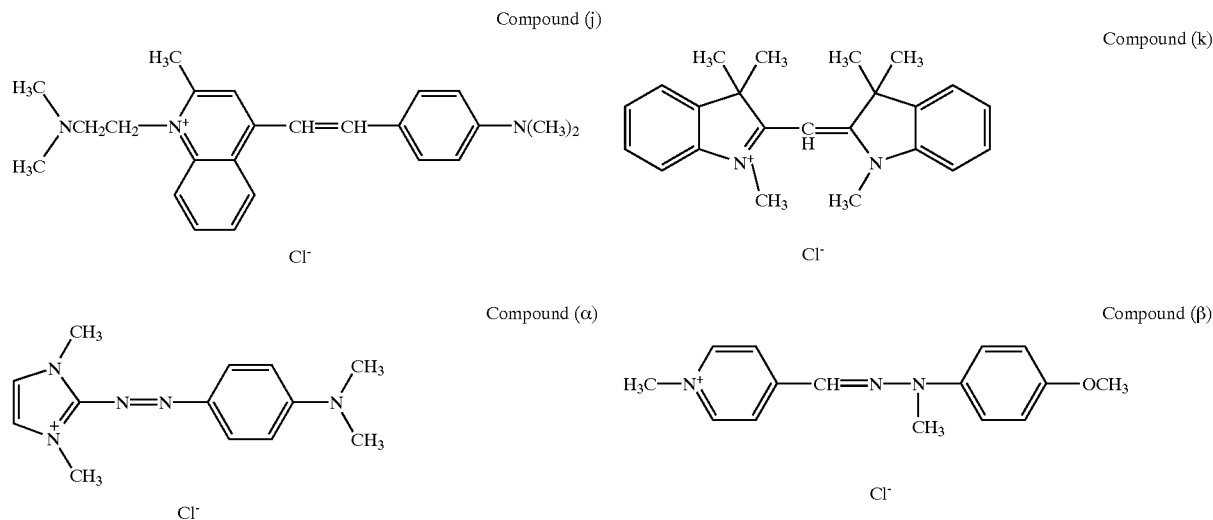

Compound (j)

Compound (k)

Compound (α)

Compound (β)

Examples 1 to 29

In a manner known per se in the art, hair dyes as shown in Tables 1 to 6 were prepared. The hair was dyed by applying, to the hair at 30° C., a dye directly when it was the dye shown in Table 1 or 3 and after mixing of components when it was the dye shown in Table 2, 4, 5 or 6, allowing to act it on the hair for 30 minutes, washing the resulting hair and drying.

Any dye composition of Examples 1 to 29 showed markedly high hair dyeing power, excellent light resistance, washing resistance, friction resistance and heat resistance and had a smaller change in color shade of the dye after storage.

TABLE 1

| Component (wt. %) | | 1 | 2 | 3 | 4 | 5 | 6 |
|---|---|---|---|---|---|---|---|
| Foam | Compound (a) | 0.5 | 0.3 | 0.3 | | | |
| | Compound (k) | | | | 0.5 | 0.3 | 0.3 |
| | Basic Red 76 | — | — | 0.1 | — | — | 0.1 |
| | HC Red 3 | — | 0.2 | — | — | 0.2 | — |
| | Monoethanolamine | 1 | 1 | 1 | 1 | 1 | 1 |
| | Ethanol | 15 | 15 | 15 | 15 | 15 | 15 |
| | Propylene glycol | 10 | 10 | 10 | 10 | 10 | 10 |
| | Polyoxyethylene (20) octyldodecyl ether | 10 | 10 | 10 | 10 | 10 | 10 |
| | Polyoxyethylene (9) tridecyl ether | 3 | 3 | 3 | 3 | 3 | 3 |
| | Polyoxyethylene (3) tridecyl ether | 6 | 6 | 6 | 6 | 6 | 6 |
| | Diethanolamide oleate | 8 | 8 | 8 | 8 | 8 | 8 |
| | Oleyl alcohol | 2 | 2 | 2 | 2 | 2 | 2 |
| | Ammonium chloride | q.s. *1 | q.s. *1 | q.s. *1 | q.s. *1 | q.s. *1 | q.s. *1 |
| | LPG (4.0 kg · cm) | 10 | 10 | 10 | 10 | 10 | 10 |
| | Purified water | Balance | Balance | Balance | Balance | Balance | Balance |

*1: amount to adjust pH to 8.5

TABLE 2

| Component (wt. %) | | 7 | 8 | 9 | 10 |
|---|---|---|---|---|---|
| First part | Compound (b) | 0.5 | 0.3 | 0.3 | 0.3 |
| | Basic Red 76 | — | — | — | 0.1 |
| | HC Red 3 | — | 0.2 | — | — |
| | p-Aminophenol | — | — | 0.2 | 0.2 |
| | p-Amino-o-cresol | — | — | 0.2 | 0.2 |
| | Ammonia (28%) | 6 | 6 | 6 | 6 |
| | Ethanol | 15 | 15 | — | — |

TABLE 2-continued

|  | Component (wt. %) | Example 7 | Example 8 | Example 9 | Example 10 |
|---|---|---|---|---|---|
| | Propylene glycol | 10 | 10 | 2 | 2 |
| | Polyoxyethylene (20) octyldodecyl ether | 10 | 10 | — | — |
| | Polyoxyethylene (40) cetyl ether | — | — | 2 | 2 |
| | Polyoxyethylene (2) cetyl ether | — | — | 2.5 | 2.5 |
| | Diethanolamide oleate | 8 | 8 | — | — |
| | Oleyl alcohol | 2 | 2 | — | — |
| | Stearyl trimethylammonium chloride | — | — | 1.5 | 1.5 |
| | Cetanol | — | — | 1.0 | 1.0 |
| | Liquid paraffin | — | — | 0.5 | 0.5 |
| | Ammonium chloride | q.s. *2 | q.s. *2 | q.s. *2 | q.s. *2 |
| | Sodium sulfite | 0.5 | 0.5 | 0.5 | 0.5 |
| | Tetrasodium ethylenediaminetetraacetate | 0.1 | 0.1 | 0.1 | 0.1 |
| | Purified water | Balance | Balance | Balance | Balance |
| Second part | Hydrogen peroxide | 6 | 6 | 6 | 6 |
| | Methy paraben | 0.1 | 0.1 | 0.1 | 0.1 |
| | Phosphoric acid | q.s. *3 | q.s. *3 | q.s. *3 | q.s. *3 |
| | Purified water | Balance | Balance | Balance | Balance |
| Third part | Ammonium persulfate (powder) | — | 2 | — | — |

*2: amount to adjust pH to 9.8,
*3: amount to adjust pH to 3.5

TABLE 3

| Component (wt. %) | Example 11 | Example 12 | Example 13 | Example 14 | Example 15 |
|---|---|---|---|---|---|
| Dye [Compound (e)] | 0.2 | | 0.15 | 0.1 | 0.2 |
| Dye [Compound (i)] | | 0.5 | | 0.1 | |
| Dye [Compound (d)] | | 0.5 | | 0.1 | 0.2 |
| Dye [Compound (α), red] | | | 0.15 | | 0.05 |
| Dye [Compound (β), yellow] | | | 0.1 | 0.1 | |
| Ethanol | | 5 | | 5 | 5 |
| Propylene glycol | | | 5 | | 5 |
| Diethylene glycol monoethyl ether | | 10 | | | |
| Guar gum | 1 | | | | |
| Hydroxypropyl guar gum | | 1 | 1 | 1 | 1 |
| "Gufquat 734" (trade name; product of ISP Japan) | 1 | 1 | | | |
| "Catinal LC100" (trade name; product of Toho Chemical Industry) | | 1 | | | 1 |
| "Polyether-modified silicone KF6005" trade name; (product of Shin-Etsu Chemical) | | | | | 0.4 |
| "Amodimethicone SM8702C" (product of Dow Corning Toray Silicone) | | | | 1.5 | |
| Monoethanolamine | | | 0.1 | | |
| Phosphoric acid | | | Amount to adjust pH to 9 | | |
| Perfume | | | q.s. | | |
| Water | | | Balance | | |
| Total (g) | | | 100 | | |

TABLE 4

|  | Component (wt. %) | Example 16 | Example 17 | Example 18 | Example 19 | Example 20 | Example 21 |
|---|---|---|---|---|---|---|---|
| 1st part | Dye [Compound (j)] | 0.2 | | 0.15 | 0.2 | | |
| | Dye [Compound (f)] | | 0.1 | 0.15 | | | |
| | Dye [Compound (k)] | | | | | 0.4 | 0.3 |
| | Dye [Compound (α), red] | | 0.1 | | 0.05 | | 0.1 |
| | 28 wt. % aqueous ammonia | | | 5 | | | |
| | Monoethanolamine | | | 2 | | | |
| | Propylene glycol | | | 8 | | | |
| | Polyoxyethylene (20) isostearyl ether | | | 24 | | | |
| | Polyoxyethylene (2) isosteary ether | | | 20 | | | |

TABLE 4-continued

|  | Component (wt. %) | Example 16 | Example 17 | Example 18 | Example 19 | Example 20 | Example 21 |
|---|---|---|---|---|---|---|---|
| | "Merquat 280" (trade name; product of Calgon Corp., 35 wt. % aqueous solution) | 8 | | | | 8 | |
| | "Polymer JR400" (trade name; product of Union Carbide) | | 0.5 | | 0.5 | | 0.5 |
| | "Amodimethicone SM8702C" (trade name; product of Dow Corning Toray Silicone) | | | 2 | | | |
| | "Polyether modified silicone KF6005" (trade name; product of Shin-Etsu Chemical) | | | | | 0.3 | 0.3 |
| | Tetrasodium ethylenediaminetetraacetate | | | | 0.1 | | |
| | Perfume | | | | q.s. | | |
| | Ammonium chloride | | | | Amount to adjust pH to 10 | | |
| | Water | | | | Balance | | |
| 2nd part | 35 wt. % aqueous hydrogen peroxide | | | | 17.1 | | |
| | Methylparaben | | | | 0.1 | | |
| | Phosphoric acid | | | | Amount to adjust pH to 3.5 | | |
| | Water | | | | Balance | | |

TABLE 5

|  | Component (wt. %) | Example 22 | Example 23 | Example 24 | Example 25 | Example 26 | Example 27 |
|---|---|---|---|---|---|---|---|
| 1st part | Toluee-2,5-diamine | 1.9 | 1 | | 1.9 | 1 | |
| | Para-aminophenol | | | 1 | | | 1 |
| | Resorcin | 2 | | | 2 | | |
| | Para-amino-ortho-cresol | | | 1.1 | | | 1.1 |
| | 2,4-Diaminophenoxyethanol | | 1.37 | | | 1.37 | |
| | Dye [Compound (g)] | 0.05 | | | 0.05 | | |
| | Dye [Compound (c)] | | 0.15 | | | | |
| | Dye [Compound (h)] | | | 0.1 | | | |
| | Dye [Compound (k)] | | | | 0.3 | 0.1 | 0.2 |
| | 28 wt. % aqueous ammonia | | | 5 | | | |
| | Monoethanolamine | | | 2 | | | |
| | Propylene glycol | | | 8 | | | |
| | Polyoxyethylene (20) | | | 24 | | | |

TABLE 5-continued

| | | Example | | | | | |
|---|---|---|---|---|---|---|---|
| Component (wt. %) | | 22 | 23 | 24 | 25 | 26 | 27 |
| | isostearyl ether | | | | | | |
| | Polyoxyethylene (2) | | | 20 | | | |
| | isostearyl ether | | | | | | |
| | "Merquat 280" (trade name; product of Calgon Corp., a 35 wt. % aqueous solution) | 8 | | | 8 | | |
| | "Polymer JR400" (product of Union Carbide) | | 0.5 | | | 0.5 | |
| | "Amodimethicone SM8702C" (trade name; product of Dow Corning Toray Silicone) | | | 2 | | | 2 |
| | Sodium sulfite | | | | 0.05 | | |
| | Ascorbic acid | | | | 0.5 | | |
| | Tetrasodium ethylenediaminetetraacetate | | | | 0.1 | | |
| | Perfume | | | | q.s. | | |
| | Ammonium chloride | | | Amount to adjust pH to 10 | | | |
| | Water | | | Balance | | | |
| 2nd part | 35 wt. % Aqueous hydrogen peroxide | | | 17.1 | | | |
| | Methylparaben | | | | 0.1 | | |
| | Phosphoric acid | | | Amount to adjust pH to 3.5 | | | |
| | Water | | | Balance | | | |

TABLE 6

| | Examples | |
|---|---|---|
| Component (wt. %) | 28 | 29 |
| First part | | |
| P-aminophenol | | 1 |
| P-amino-o-cresol | | 1.1 |
| Compound (i) | 0.1 | |
| Compound (a) | | 0.2 |
| 28 wt. % aqueous ammonia | 5 | |
| Monoethanolamine | 2 | |
| Cetanol | 8.5 | |
| Polyoxyethylene (40) cetyl ether | 3 | |
| Polyoxyethylene (2) cetyl ether | 3.5 | |
| Stearyl trimethyl ammonium chloride | 2 | |
| Liquid paraffin | 0.5 | |
| Sodium sulfite | 0.05 | |
| Ascorbic acid | 0.5 | |
| Tetrasodium ethylenediaminetetraacetate | 0.1 | |
| Perfume | q.s. | |
| Ammonium chloride | Amount to adjust pH to 10 | |
| Water | Balance | |
| Second part | | |
| 35 wt. % aqueous hydrogen peroxide | 17.1 | |
| Methylparaben | 0.1 | |
| Phosphoric acid | Amount to adjust pH to 3.5 | |
| Water | Balance | |

What is claimed is:

1. A hair dye composition comprising, a direct dye compound of formula (1):

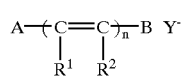
(1)

wherein, $R^1$ and $R^2$ each independently represent a hydrogen atom or a $C_{1-6}$ alkyl group which may have a substituent;

A represents a group of formula (2):

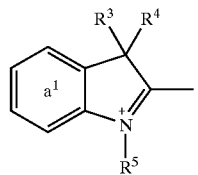
(2)

wherein $R^3$, $R^4$ and $R^5$ each independently represent a $C_{1-6}$ alkyl group which may have a substituent, or $R^4$ and $R^5$ may be coupled together to form a cyclic structure, benzene ring $a^1$ may have a substituent other than a sulfonic acid group or may be condensed with an aromatic ring, or A is a group of formula (3):

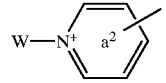
(3)

wherein W represents an aralkyl group, a carbamoylalkyl group or $—T—NR^6R^7$, wherein $R^6$ and $R^7$ each independently represent a $C_{1-6}$ alkyl group which may have a substituent, an aromatic group which may have a substituent or a heterocyclic group which may have a substituent, or $R^6$ and $R^7$ may form a heterocyclic ring together with the adjacent nitrogen atom, and T represents a divalent linear $C_{1-4}$ hydrocarbon group which may have a substituent, pyridine ring $a^2$ may be condensed with an aromatic ring, B represents a group represented by the formula $—Z^1$, $—NR^8—Z^1$ or $—CH=Z^2$ wherein when A is a group of formula (3) $Z^1$ represents an aromatic or heterocyclic aromatic group which may have a substituent, $R^8$ represents a hydrogen atom, a $C_{1-4}$ alkyl group which may have a substituent or an aromatic group which may have a substituent or $R^8$ and $Z^1$ may be coupled together to form a nitrogen-containing heterocyclic group which may have a substituent, $Z^2$ represents a divalent group obtained by removing two hydrogen atoms from the methylene group on the ring of a heterocyclic aromatic compound which may have a substituent, wherein when A is a group of formula (2) $R^8$ represents a hydrogen atom, a $C_{1-4}$ alkyl group which may have a substituent or an aromatic group which may have a substituent or $R^8$ and $Z^1$ may be coupled together to form a nitrogen-containing heterocyclic group which may have a substituent, $Z^2$ represents a divalent group obtained by removing two hydrogen atoms from the methylene group on the ring of a heterocyclic aromatic compound which may have a substituent, and $Z^1$ may have a substituent and is selected from the group consisting of

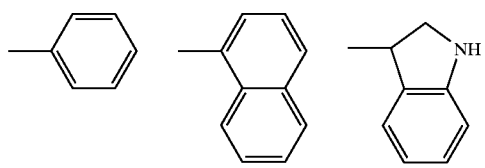

-continued

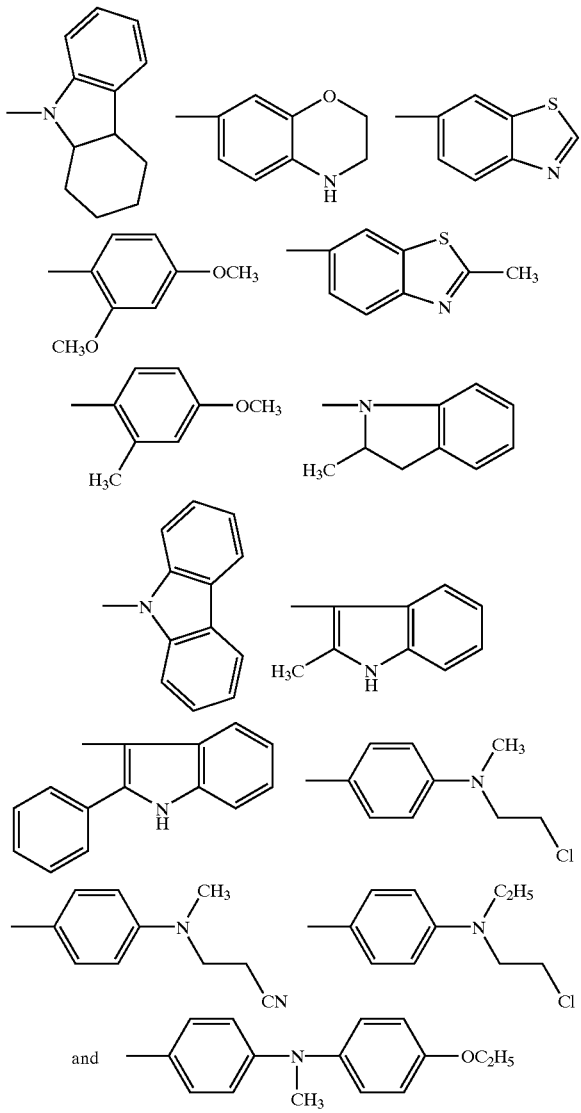

with the proviso that when A is a group of formula (2), B represents the group —Z¹ and Z¹ represents an aromatic group or when A is a group of formula (2), B represents the group —CH=Z², Z² represents an indolinidene group and n does not stand for 0, the aromatic group or indolinidene group has at least one substituent represented by the formula: —NR⁹R¹⁰ wherein R⁹ represents a $C_{1-4}$ alkyl group having as a substituent a chlorine atom or a cyano, an acylamino, an alkoxy, a monoalkylamino, a dialkylamino, a trimethylammoniumyl group, or a phenyl group which may have a substituent and R¹⁰ represents a $C_{1-6}$ alkyl group which may have a substituent, n stands for an integer of 0 to 3, wherein when B represents the group —Z¹ or group —NR⁸—Z¹ n is 1 to 3 and when B represents the group —CH=Z² n is 0 to 3; and $Y^{31}$ stands for an anion.

2. The hair dye composition according to claim 1, further comprising an oxidizing agent.

3. The hair dye composition according to claim 1, further comprising an oxidation dye.

4. The hair dye composition according to claim 1, wherein A in formula (1) represents a group of formula (2).

5. The hair dye composition according to claim 1, wherein the compound of formula (1) is represented by formula (4):

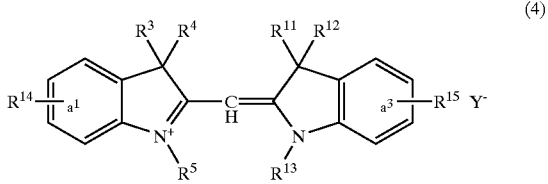

(4)

wherein, $R^3$, $R^4$, $R^5$, $R^{11}$, $R^{12}$ and $R^{13}$ each independently represent a $C_{1-6}$ alkyl group which may have a substituent; $R^{14}$ and $R^{15}$ each independently represent a hydrogen atom, a $C_{1-6}$ alkyl group which may be substituted by a hydroxyl group, a $C_{1-6}$ alkoxy group, a halogen atom, a $C_{2-7}$ alkoxycarbonyl group, a carboxy group or salt thereof, a $C_{1-6}$ acylamino group, an amino group which may be substituted with one or two $C_{1-6}$ alkyl groups which may be substituted by a hydroxyl group, a nitro group, a hydroxyl group or a $C_{1-6}$ acyl group; benzene rings $a^1$ and $a^3$ may each be cyclocondensed with an aromatic ring; and $Y^-$ represents an anion.

6. A method for dyeing the hair comprising
applying the hair dye composition of claim 1 to the hair;
allowing the hair dye composition to act on the hair for a time and under conditions suitable for dying;
removing the hair dye composition from the hair.

7. The hair dye composition according to claim 1, wherein $R^6$ or $R^7$ may be a group of:

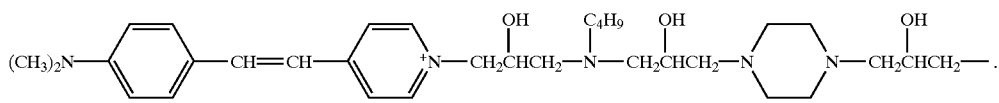

8. The hair dye composition according to claim 2, wherein the oxidizing agent is selected from the group consisting of hydrogen peroxide, ammonium persulfate, potassium persulfate, sodium persulfate, sodium perborate, sodium percarbonate, sodium bromate, and potassium bromate.

9. The hair dye composition according to claim 2, wherein the oxidizing agent comprises 0.5 to 10% by weight of the total composition.

10. The hair dye composition according to claim 3, wherein the oxidation dye comprises 0.01 to 20% by weight of the total composition.

11. The hair dye composition according to claim 1, wherein the direct dye comprises 0.01 to 20% by weight of the total composition.

12. The hair dye composition according to claim 1, further comprising an alkali agent.

13. The hair dye composition according to claim 1, wherein the alkali agent comprises 0.02 to 20% by weight of the total composition.

14. The hair dye composition according to claim 1, further comprising an autoxidation dye, a nitro dye, or a disperse dye.

15. The hair dye composition according to claim 1, further comprising an anionic surfactant or an anionic polymer.

16. The hair dye composition according to claim 1, further comprising a polyol, a polyol alkyl ether, a cationic polymer, a amphoteric polymer, or silicone.

17. A hair dye composition comprising, a direct dye compound selected from the group consisting of

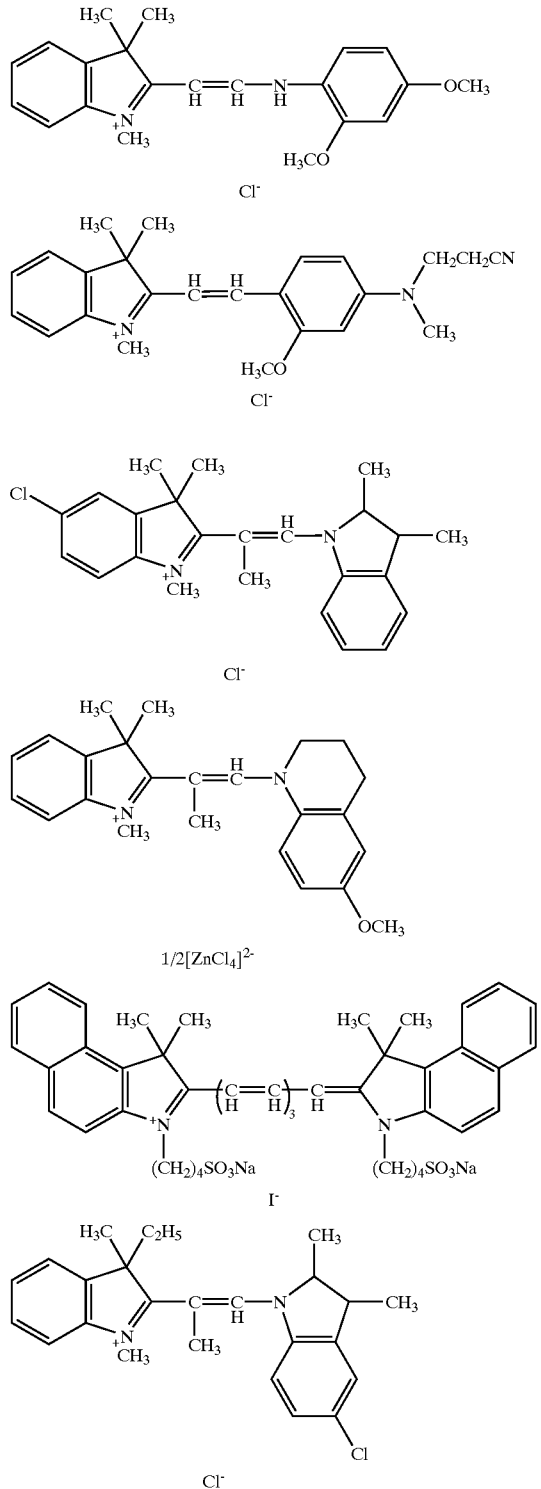
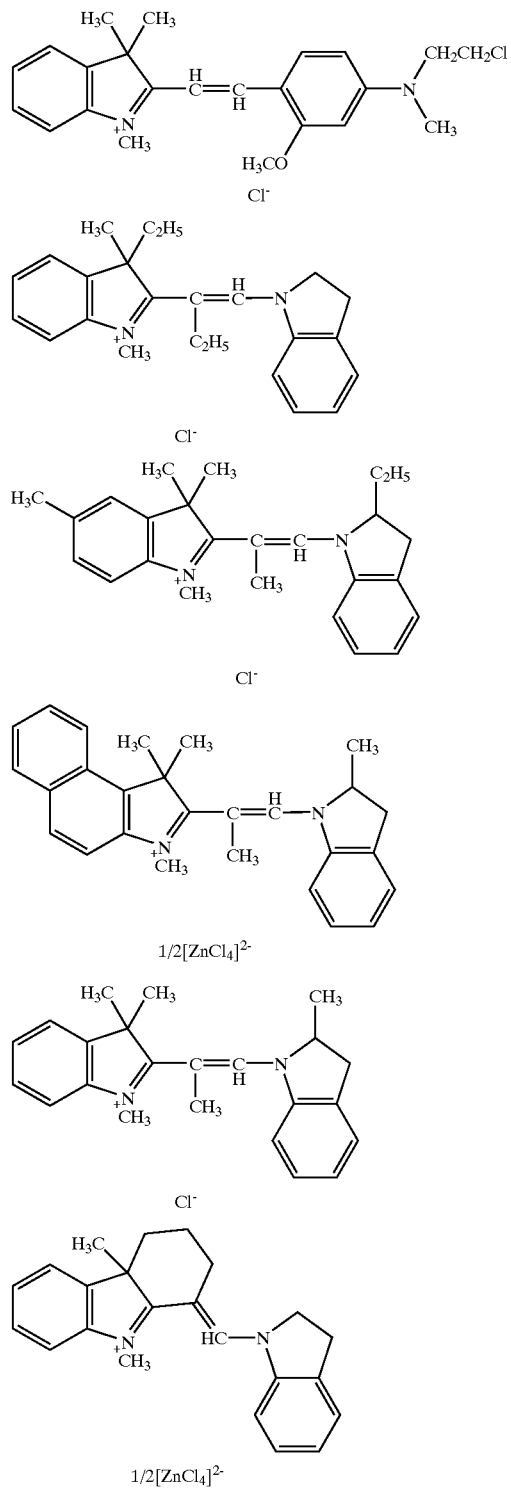

-continued
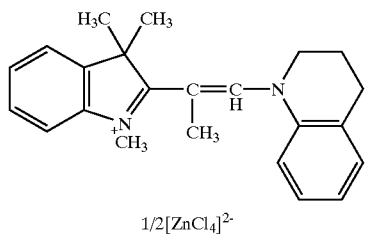
1/2[ZnCl₄]²⁻
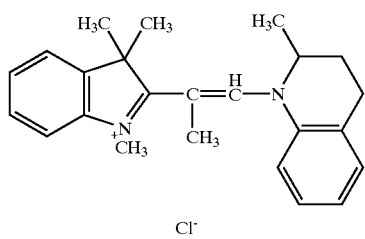
Cl⁻
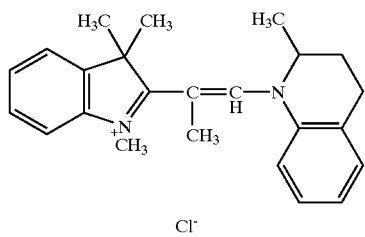
Cl⁻
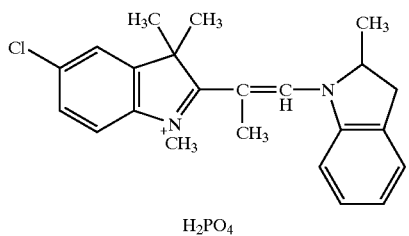
H₂PO₄⁻
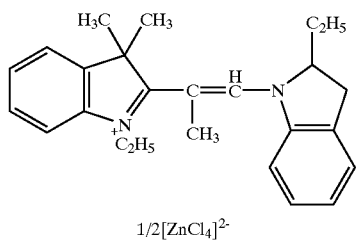
1/2[ZnCl₄]²⁻
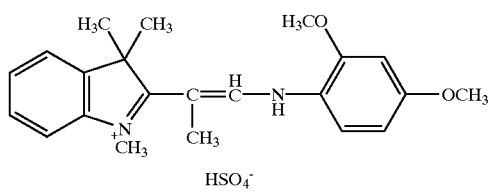
HSO₄⁻
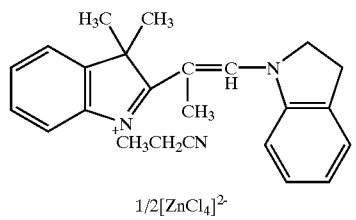
1/2[ZnCl₄]²⁻
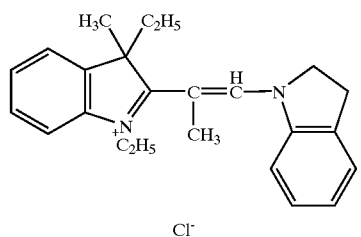
Cl⁻
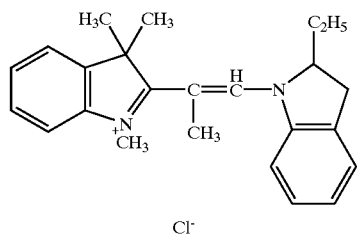
Cl⁻
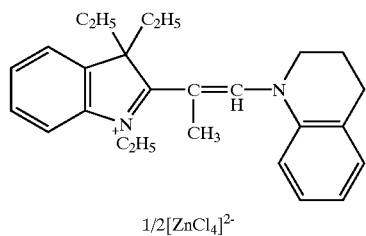
1/2[ZnCl₄]²⁻
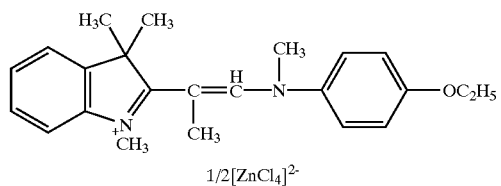
1/2[ZnCl₄]²⁻
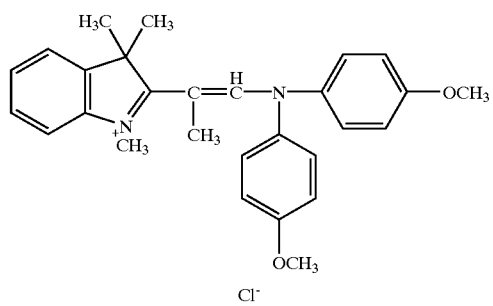
Cl⁻

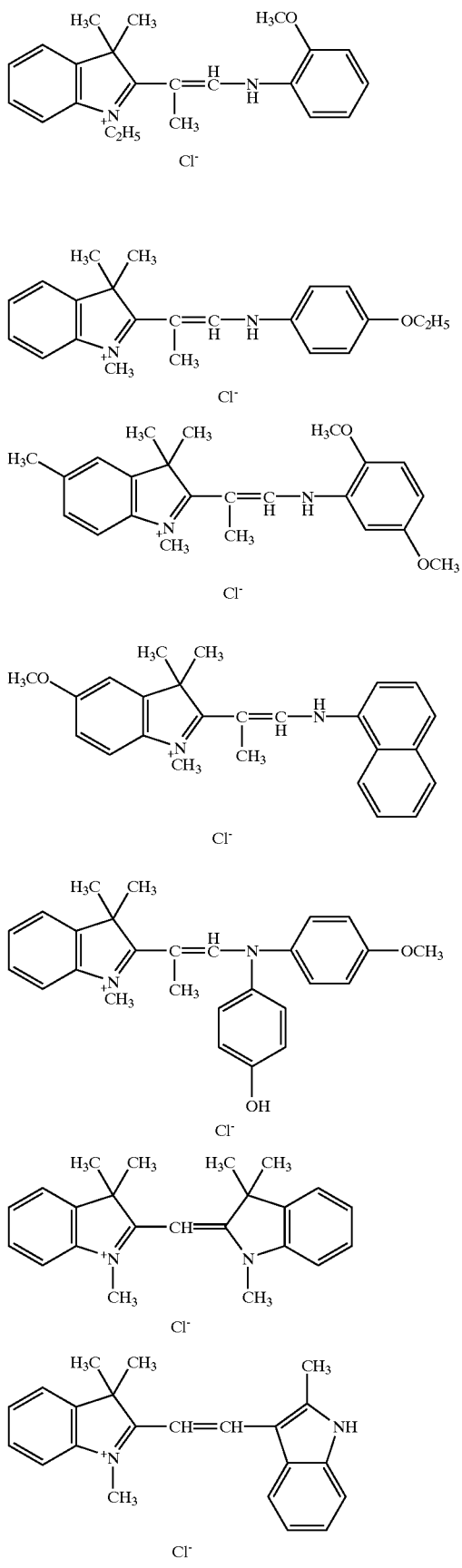

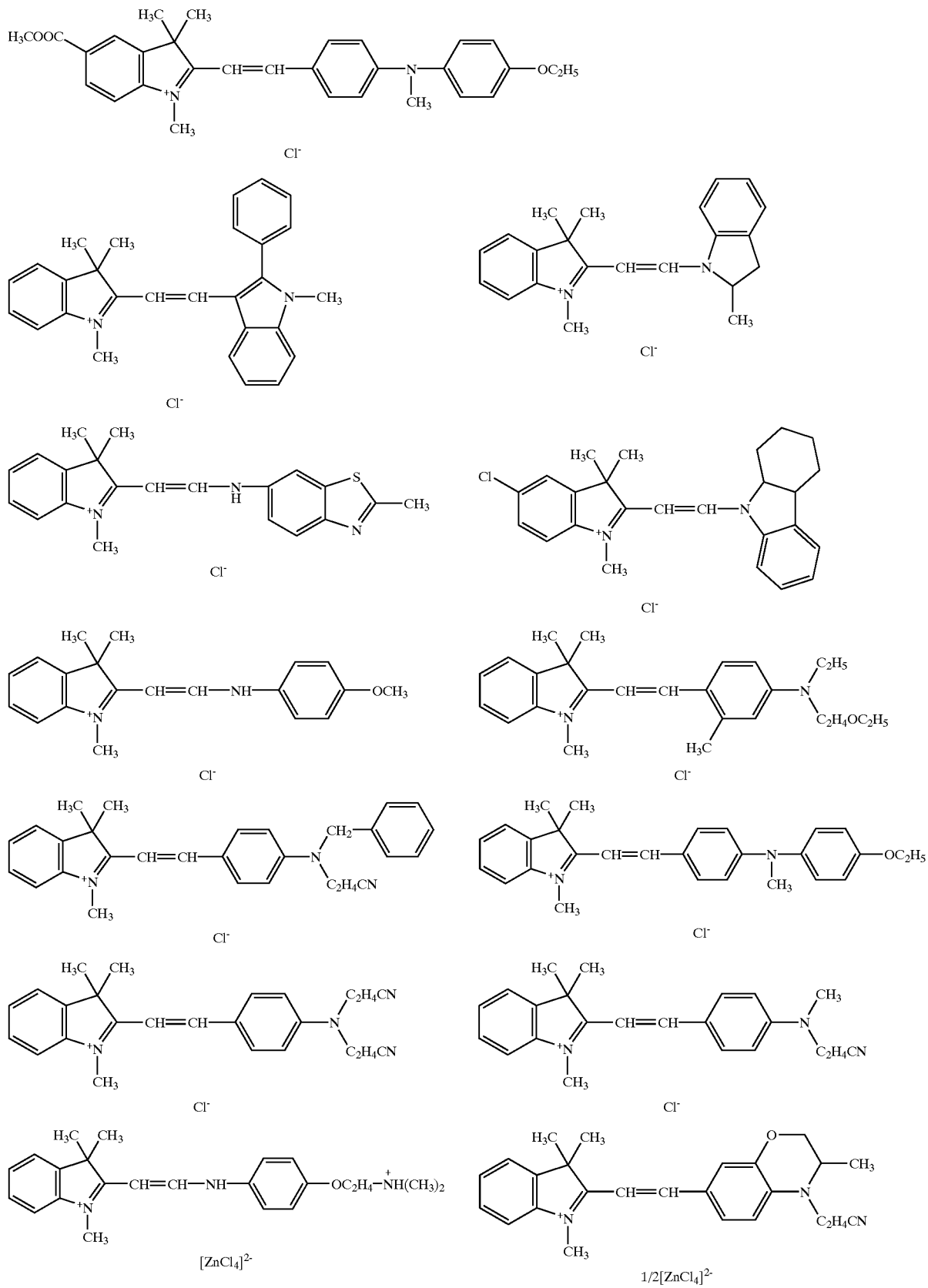

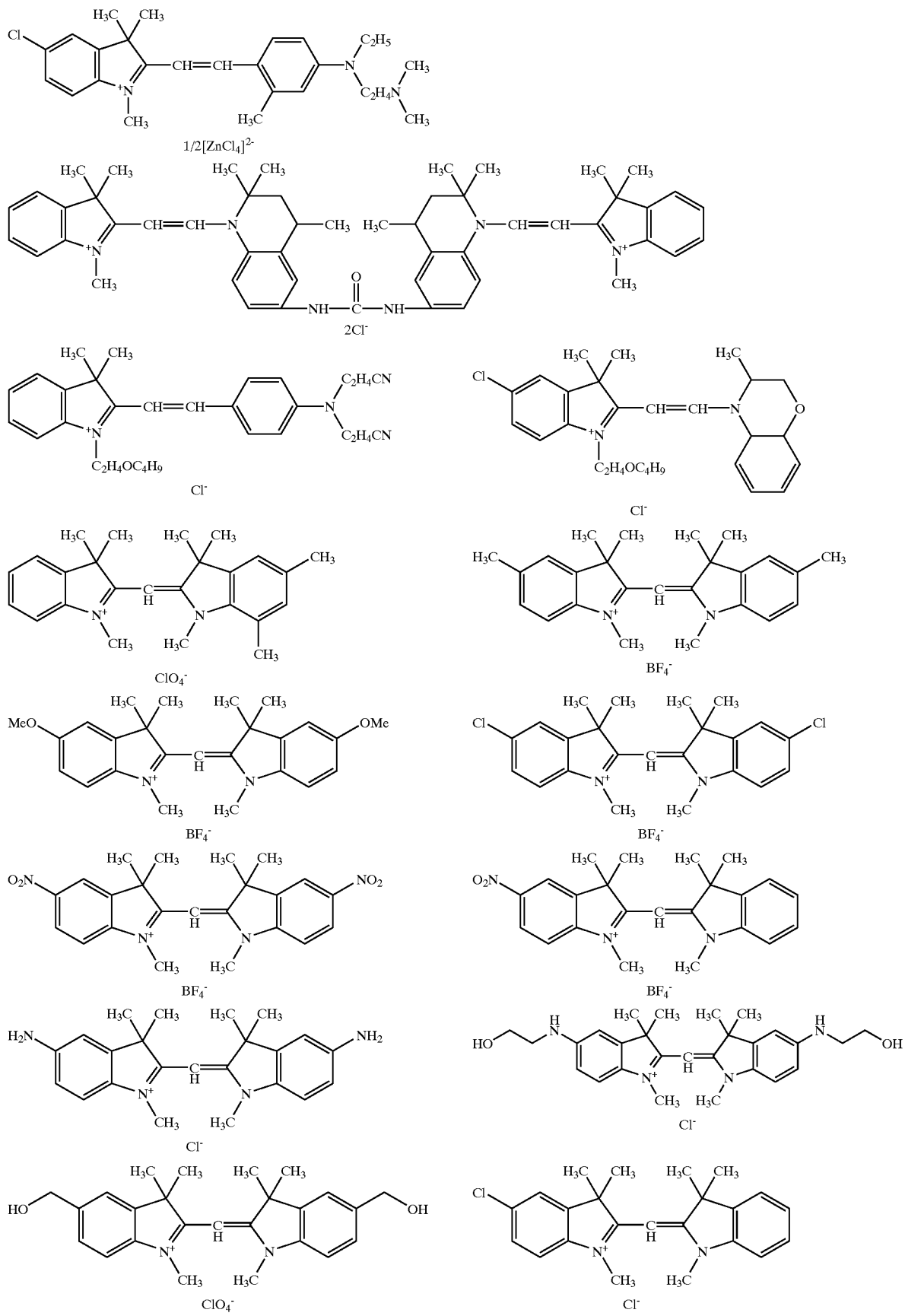

-continued
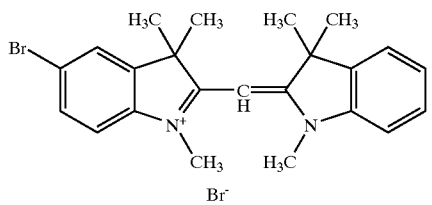
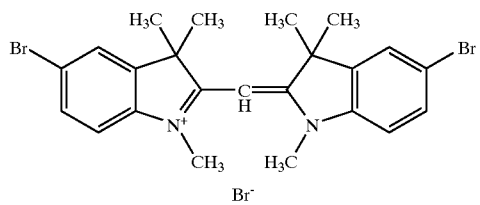
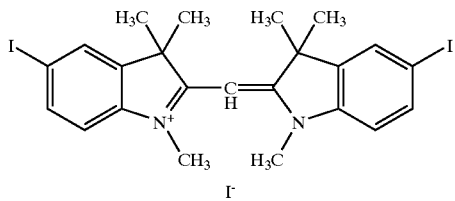
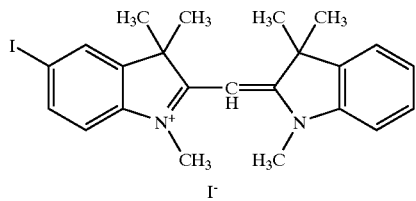
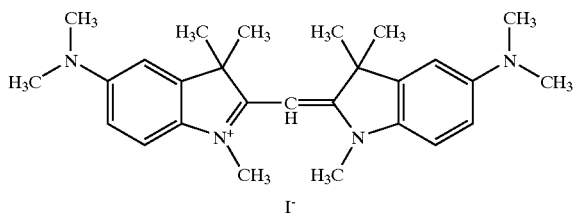
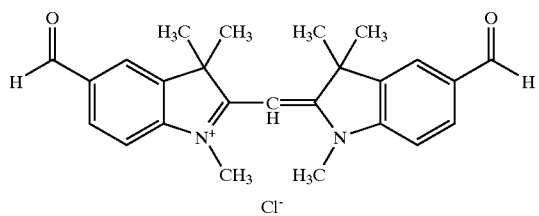
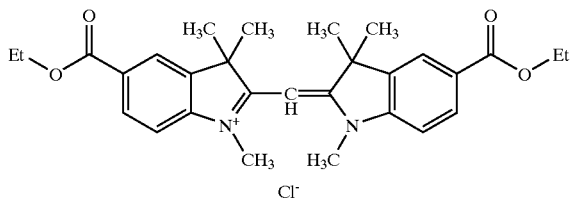
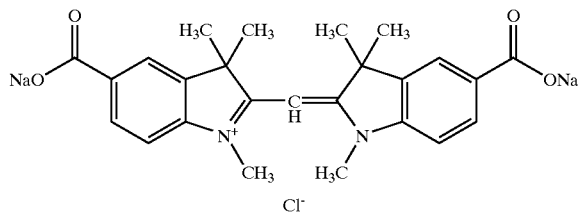
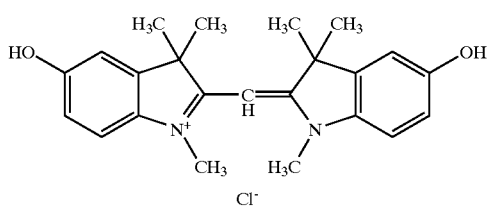
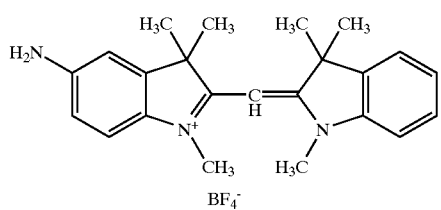
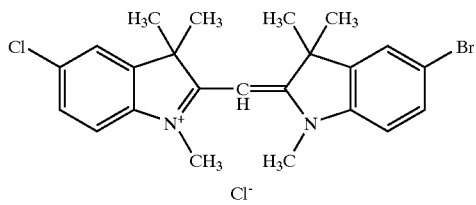
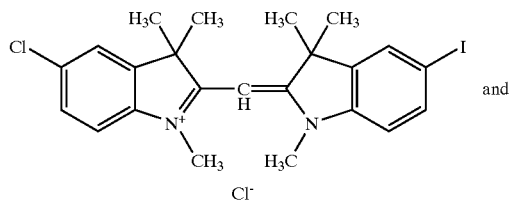
and
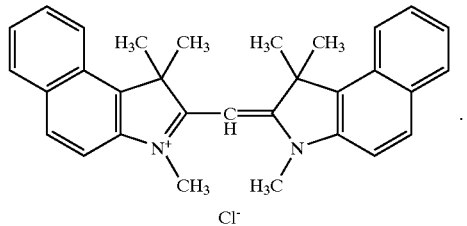

18. A hair dye composition comprising, a direct dye compound selected from the group consisting of
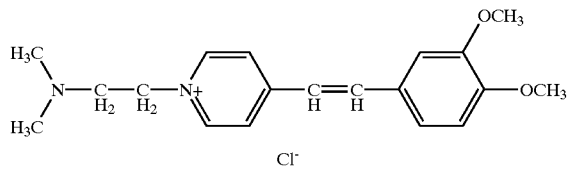
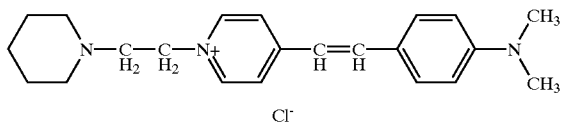
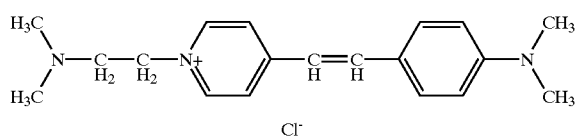
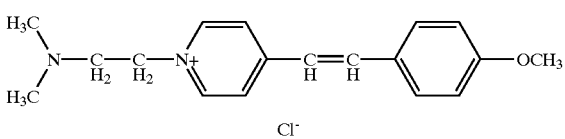
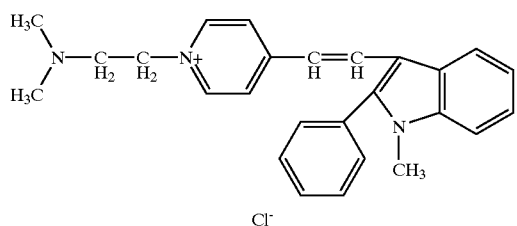
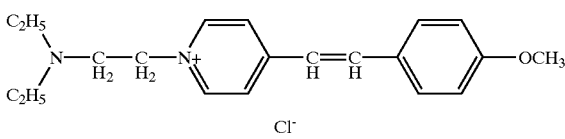
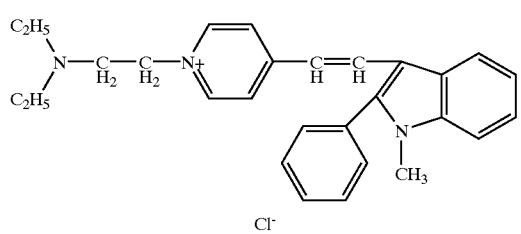
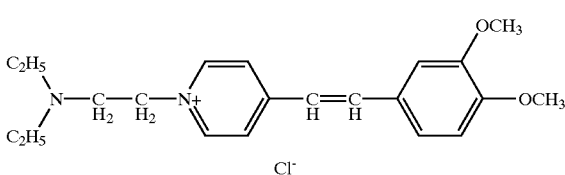
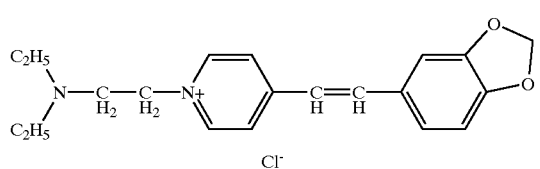
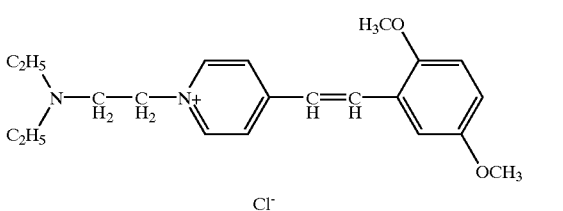
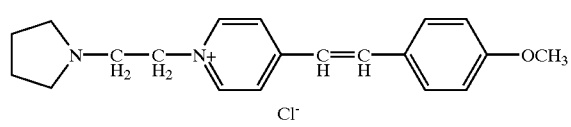
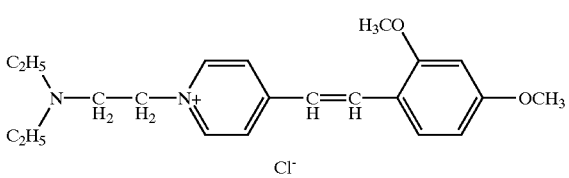
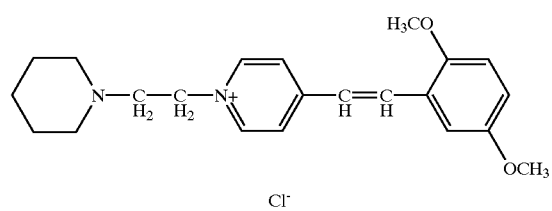
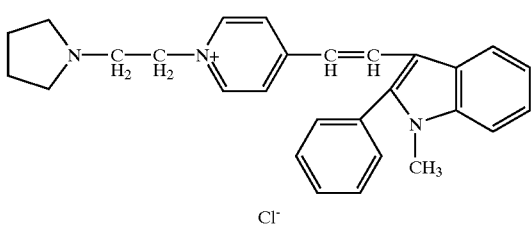
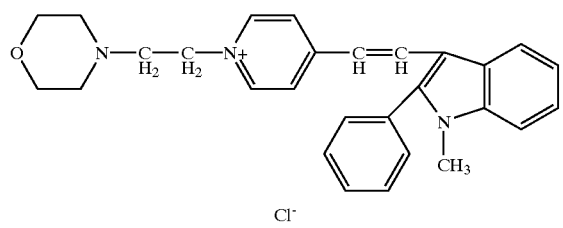
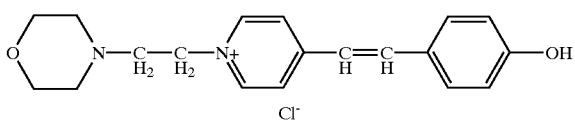

-continued
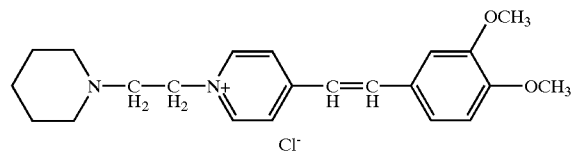
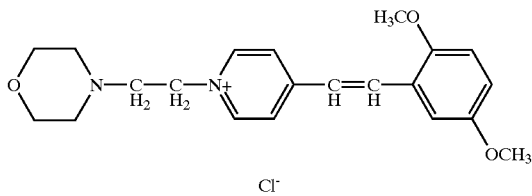
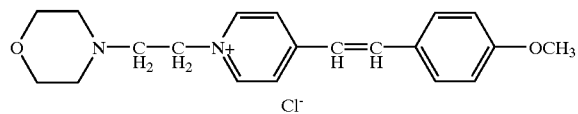
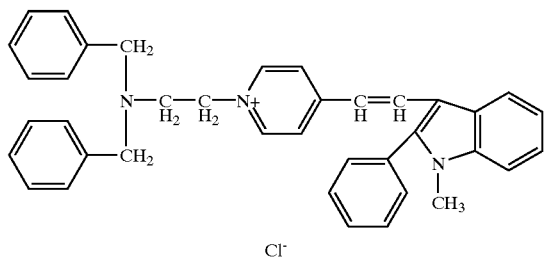
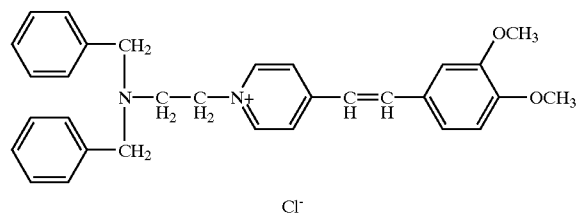
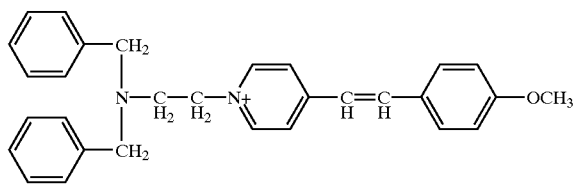
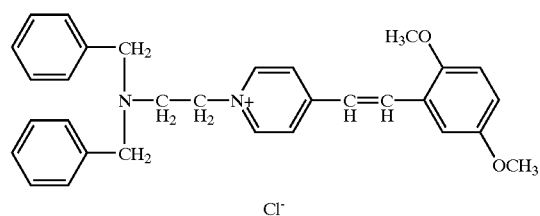
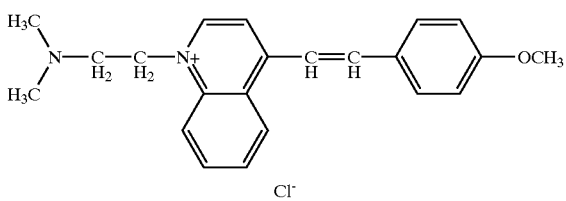
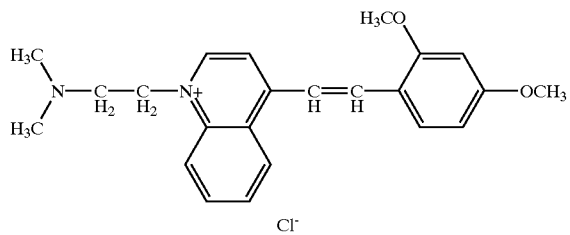
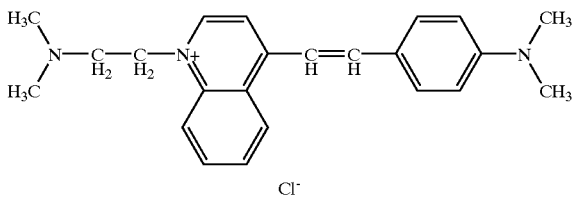
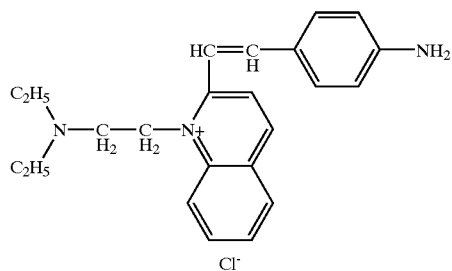
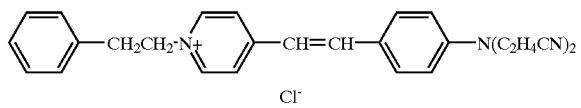
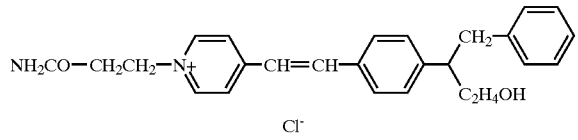
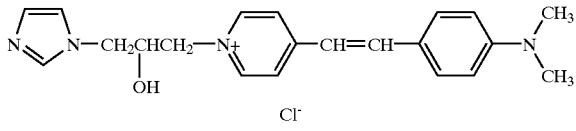
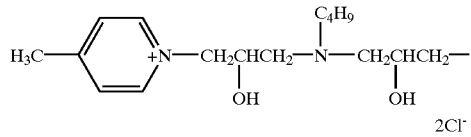
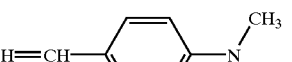

-continued
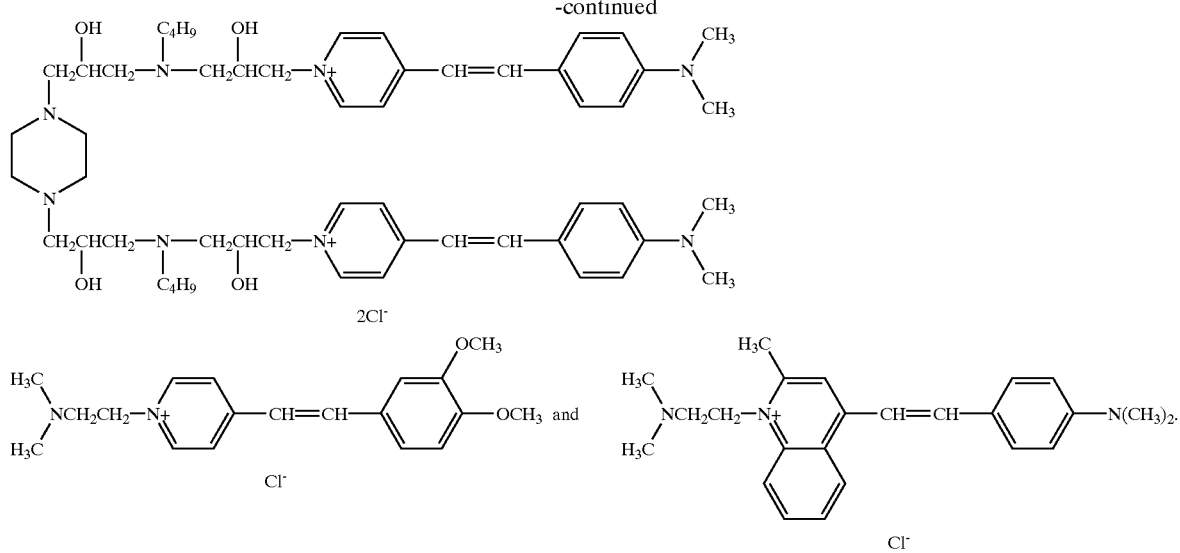
19. The method according to claim 6, wherein the time is 1 to 60 minutes.
20. The method according to claim 6, wherein the conditions suitable for dying is a temperature of 10 to 50° C.
* * * * *

UNITED STATES PATENT AND TRADEMARK OFFICE
CERTIFICATE OF CORRECTION

PATENT NO. : 6,547,834 B1
DATED : April 15, 2003
INVENTOR(S) : Kenichi Matsunaga et al.

It is certified that error appears in the above-identified patent and that said Letters Patent is hereby corrected as shown below:

Column 34,
Line 12, "$R^5$" should read -- $R^1$ --

Column 42,
Third formula, "
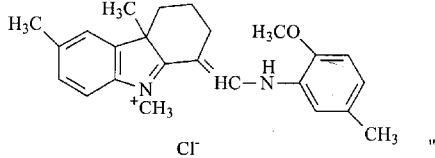
should read --
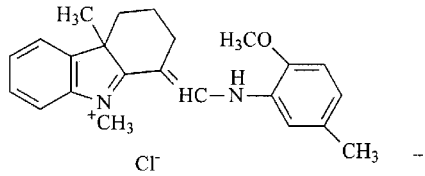
--

Column 51,
Seventh formula "
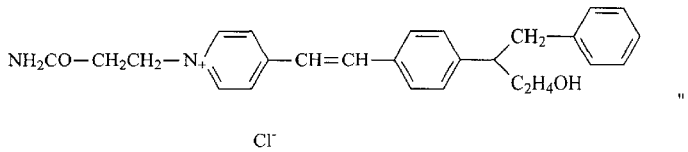
"
should read --
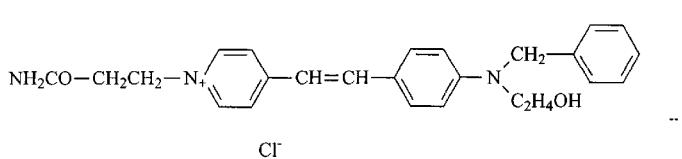
--

Signed and Sealed this

Sixteenth Day of September, 2003

JAMES E. ROGAN
*Director of the United States Patent and Trademark Office*